(12) United States Patent
Okazaki

(10) Patent No.: US 8,998,801 B2
(45) Date of Patent: Apr. 7, 2015

(54) INSERTION INSTRUMENT

(71) Applicant: Olympus Medical Systems Corp., Tokyo (JP)

(72) Inventor: Tsugio Okazaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/101,696

(22) Filed: Dec. 10, 2013

(65) Prior Publication Data

US 2014/0165772 A1 Jun. 19, 2014

Related U.S. Application Data

(63) Continuation of application No. PCT/JP2013/062186, filed on Apr. 25, 2013.

(30) Foreign Application Priority Data

Jul. 2, 2012 (JP) .................................. 2012-148709

(51) Int. Cl.
*A61B 1/00* (2006.01)
*B25J 18/06* (2006.01)
*G02B 23/24* (2006.01)
*A61B 1/005* (2006.01)

(52) U.S. Cl.
CPC ............. *B25J 18/06* (2013.01); *G02B 23/2476* (2013.01); *A61B 1/0057* (2013.01)

(58) Field of Classification Search
USPC .................................................. 600/146–152
See application file for complete search history.

(56) References Cited

U.S. PATENT DOCUMENTS

| | | | | |
|---|---|---|---|---|
| 3,557,780 A * | 1/1971 | Sato | | 600/141 |
| 3,610,231 A * | 10/1971 | Takahashi et al. | | 600/139 |
| 3,799,151 A * | 3/1974 | Fukaumi et al. | | 600/142 |
| 4,078,555 A * | 3/1978 | Takahashi | | 600/148 |
| 4,203,430 A * | 5/1980 | Takahashi | | 600/149 |
| 4,351,323 A * | 9/1982 | Ouchi et al. | | 600/142 |
| 4,748,969 A * | 6/1988 | Wardle | | 600/150 |
| 5,167,221 A * | 12/1992 | Chikama | | 600/149 |
| 5,174,276 A * | 12/1992 | Crockard | | 600/104 |
| 5,179,935 A * | 1/1993 | Miyagi | | 600/142 |
| 5,810,715 A | 9/1998 | Moriyama | | |
| 5,976,074 A | 11/1999 | Moriyama | | |
| 6,811,532 B2 * | 11/2004 | Ogura et al. | | 600/146 |
| 8,133,171 B2 * | 3/2012 | Barry et al. | | 600/151 |

(Continued)

FOREIGN PATENT DOCUMENTS

| | | |
|---|---|---|
| EP | 2 446 802 A1 | 5/2012 |
| JP | 04-102433 A | 4/1992 |

(Continued)

*Primary Examiner* — Matthew J Kasztejna
(74) *Attorney, Agent, or Firm* — Scully, Scott, Murphy & Presser, PC

(57) ABSTRACT

Contact between a face to be pressed and a cam face in an interaxial direction T of two inner guide sheaths is set so that a contact width H therebetween is shorter than an interaxial distance L, and so that the contact position is located between axes of the two inner guide sheaths. As a result, even in a case where external diameters of two inner guide sheaths that form a pair are slightly different to each other, a braking member can be tilted to cause a contact face to simultaneously come in contact with the respective inner guide sheaths, and a pressing force from an eccentric cam can be transmitted equally to the respective inner guide sheaths.

13 Claims, 26 Drawing Sheets

(56) References Cited

U.S. PATENT DOCUMENTS

| | | | |
|---|---|---|---|
| 8,366,606 B2* | 2/2013 | Watanabe et al. | 600/144 |
| 2002/0017515 A1* | 2/2002 | Obata et al. | 219/137 R |
| 2002/0177750 A1* | 11/2002 | Pilvisto | 600/146 |
| 2004/0242966 A1* | 12/2004 | Barry et al. | 600/146 |
| 2006/0200000 A1* | 9/2006 | Sato et al. | 600/146 |
| 2009/0143647 A1* | 6/2009 | Banju | 600/149 |
| 2011/0282153 A1 | 11/2011 | Ueki | |

FOREIGN PATENT DOCUMENTS

| | | |
|---|---|---|
| JP | 09-294710 A | 11/1997 |
| JP | 4856289 B2 | 1/2012 |
| WO | WO 2011/092937 A1 | 8/2011 |

* cited by examiner

INSERTION INSTRUMENT

CROSS REFERENCE TO RELATED APPLICATION

This application is a continuation application of PCT/JP2013/062186 filed on Apr. 25, 2013 and claims benefit of Japanese Application No. 2012-148709 filed in Japan on Jul. 2, 2012, the entire contents of which are incorporated herein by this reference.

BACKGROUND OF THE INVENTION

1. Field of the Invention

The present invention relates to an insertion instrument having an elongated insertion portion that is inserted into a subject and an operation portion, in which an action portion that acts in accordance with an operation input from the operation portion is provided in the insertion portion.

2. Description of the Related Art

In recent years, an insertion instrument, for example, an endoscope, that is inserted inside a subject or an object has been widely used in the medical field and the industrial field. An endoscope used in the medical field observes an organ inside a body cavity of a subject by inserting an elongated insertion portion into the body cavity. As necessary, the endoscope can perform various kinds of treatment using a treatment instrument that is inserted inside a treatment instrument insertion channel provided in the endoscope.

Further, with an endoscope used in the industrial field, by inserting an elongated insertion portion of the endoscope inside an object such as a jet engine or pipes of a factory, it is possible to carry out an inspection to observe flaws or corrosion or the like at a site to be examined inside the object and perform various repairs.

A configuration is known in which an action portion, for example, a bending portion that is bendable in a plurality of directions, is provided in an insertion portion of an endoscope. The bending portion improves the advancing ability of the insertion portion at a curved section inside a duct, and also varies an observation direction of an observation optical system provided in a distal end portion that is positioned further on a distal end side in the insertion direction (hereunder, referred to simply as "distal end side") than the bending portion in the insertion portion.

Normally, a bending portion provided in an insertion portion of an endoscope is configured to be bendable in, for example, four directions, namely, upward, downward, left, and right, by connecting a plurality of bending pieces along the insertion direction of the insertion portion. Further, the bending portion is configured to be bendable in any of the upward, downward, left, and right directions by performing a pulling operation from an operation portion with respect to any of four wires that are linear members that are inserted into the insertion portion and which are movable forward and rearward in the insertion direction and whose distal ends are fixed to a bending piece positioned furthest on the distal end side among the bending pieces.

As such a kind of endoscope, for example, Japanese Patent No. 4856289 discloses a configuration in which: a first bending portion and a second bending portion are provided on a distal end side of an insertion portion; the outer circumference of four wires that are inserted through the insertion portion are respectively covered by an inner guide sheath (inner guide pipe) that is a linear member that is movable forward and rearward in an insertion direction; a distal end in the insertion direction of the inner guide sheath is fixed to a distal end of the second bending portion; proximal ends in the insertion direction of the respective inner guide sheaths are configured so as to be simultaneously switchable between a fixed state and a non-fixed state by a fixing switching member (linear member fixing mechanism); the outer circumference of each inner guide sheath is covered by an outer guide sheath (outer guide pipe), respectively; distal ends of the outer guide sheaths are fixed to a distal end of a flexible tube portion; and proximal ends of the outer guide sheaths are fixed at a more rearward position than the proximal end of the flexible tube portion.

According to this configuration, it is possible to cause the first bending portion and the second bending portion to bend in a manner that takes the distal ends of the outer guide sheaths as a starting point by operating a bending operation knob to pull a wire in a state in which a fixed state of the proximal ends of the respective inner guide sheaths has been released. On the other hand, it is possible to cause only the first bending portion to bend in a manner that takes the distal ends of the inner guide sheaths as a starting point by operating the linear member fixing mechanism and performing an operation with respect to the bending operation knob to pull a wire in a state in which the proximal ends of the respective inner guide sheaths are simultaneously in a fixed state. Therefore, the length of the bending portion can be easily varied according to the usage situation, and the insertability of the insertion portion can be improved with a simple configuration.

According to the technology disclosed in Japanese Patent No. 4856289, the linear member fixing mechanism is configured to include a substrate and two moving members that are movable in contacting and separating directions with respect to two faces (top face and bottom face) of the substrate. The linear member fixing mechanism actuates each moving member through a link mechanism, and it is possible to fix the respective inner guide sheaths by each moving members sandwiching the proximal end portions (more specifically, a pipe stopper) of two inner guide sheaths between the moving member and the substrate with a predetermined pressing force, respectively.

SUMMARY OF THE INVENTION

An insertion instrument according to one aspect of the present invention includes: an insertion portion for inserting into a subject; an operation portion that is provided on a proximal end side of the insertion portion; an action portion that is provided in the insertion portion and that acts in accordance with an operation input with respect to the operation portion; two linear members that are adjacent and that move in a longitudinal axis direction of the insertion portion in response to the operation input at the operation portion to transmit the operation input at the operation portion to the action portion; a braking member that includes a contact face for contacting the two linear members, and which is disposed in a state in which the braking member is movable in an approximately perpendicular direction with respect to a movement direction and an interaxial direction of the two linear members and in which the contact face is tiltable; a face to be pressed that is provided on a rear face side of the contact face of the braking member; and a pressing member for pressing the face to be pressed in the approximately perpendicular direction.

DETAILED DESCRIPTION OF THE PREFERRED EMBODIMENTS

Figure 1:
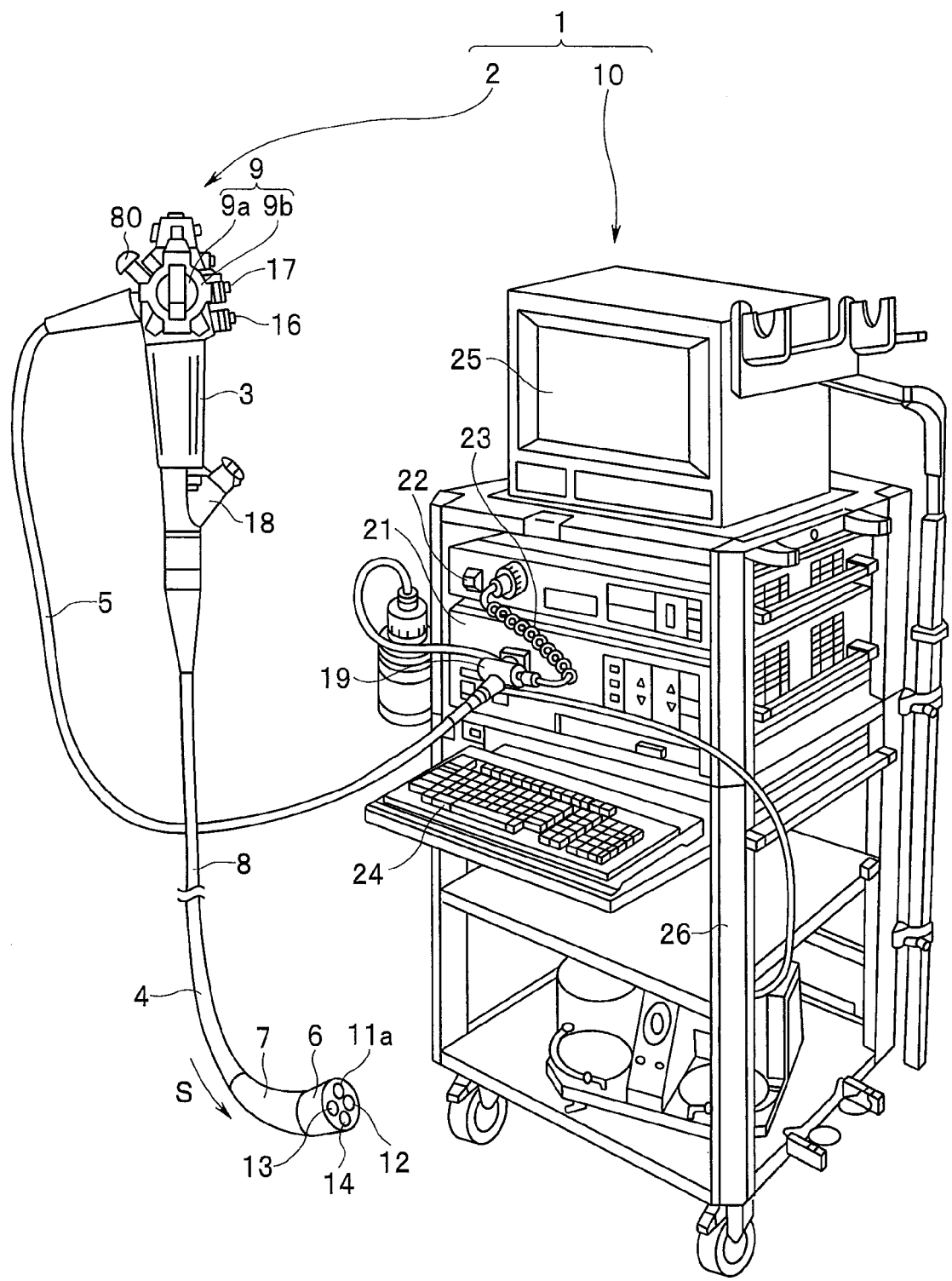
FIG. 1 is a perspective view that illustrates the external appearance of an endoscope apparatus including an endoscope according to a first embodiment of the present invention.

A first embodiment with respect to an endoscope as one example of an insertion instrument is described hereunder with reference to the drawings. FIG. 1 is a perspective view that illustrates the external appearance of an endoscope apparatus including an endoscope according to the present embodiment.

As shown in FIG. 1, an endoscope apparatus 1 includes an endoscope 2 and a peripheral apparatus 10 as principal components. The endoscope 2 includes an insertion portion 4 that is inserted into a subject, an operation portion 3 that is connected to a proximal end side of the insertion portion 4, a universal cord 5, and a connector 19 as principal components.

The peripheral apparatus 10 includes, as principal components, a light source apparatus 21, a video processor 22, a connection cable 23, a keyboard 24, and a monitor 25, all of which are placed on a stand 26. The endoscope 2 and the peripheral apparatus 10 configured as described above are connected to each other by the connector 19.

The operation portion 3 of the endoscope 2 is provided with bending operation knobs 9, an air/water feeding operation button 16, a suction operation button 17, a treatment instrument insertion port 18, and a rotatable fixing lever 80 that is an operation member. Note that the bending operation knobs 9 are constituted by an upward/downward bending operation knob 9a and a leftward/rightward bending operation knob 9b.

The insertion portion 4 of the endoscope 2 is formed in an elongated shape along an insertion direction S, and is constituted by, in order from the distal end side, a distal end portion 6, a bending portion 7 that is bendable in a plurality of directions that is an action portion connected to the proximal end side of the distal end portion 6, and a flexible tube portion 8 that is connected to the proximal end side of the bending portion 7.

Note that, depending on the specifications and the like of the endoscope 2, in some cases the operation portion 3 is connected in a state in which the longitudinal axis direction thereof is inclined by approximately several degrees with respect to the longitudinal axis direction (insertion direction S) of the insertion portion 4. However, according to the present invention, in this case also, the two longitudinal axis directions are regarded as being substantially the same. That is, according to the present invention, the term "longitudinal axis direction S of the insertion portion 4" is assumed to have a broad meaning that also includes the longitudinal axis direction of the entire endoscope 2.

The bending portion 7 is caused to operate, that is, bend, by an operation input with respect to the bending operation knobs 9 provided on the operation portion 3. The bending portion 7 is configured to be bendable in, for example, four directions, namely, upward, downward, left and right, accompanying pulling/relaxing of wires 30 (see FIG. 2), described below, that are inserted through the insertion portion 4, in accordance with a bending operation of the bending operation knobs 9.

An objective lens 11a of an unshown image pickup unit that is provided inside the distal end portion 6 is provided in a distal end face on the distal end side of the distal end portion 6. A distal end opening 12 of an unshown channel that supplies a fluid towards a site to be examined inside the subject, an illuminating window 13 for illuminating the inside of the subject, and a distal end opening 14 of an unshown treatment instrument insertion channel are also provided in the distal end face of the distal end portion 6.

A gas or a liquid is selectively ejected from the distal end opening 12 in accordance with an operation of the air/water feeding operation button 16 of the operation portion 3. Mucus and the like in a body cavity is selectively recovered from the distal end opening 14 via the treatment instrument insertion channel in accordance with an operation of the suction operation button 17 of the operation portion 3. Further, various kinds of treatment instruments that are inserted from the treatment instrument insertion port 18 are projected out from the distal end opening 14 towards a site to be examined.

The connector 19 is provided at the distal end of the universal cord 5 of the endoscope 2. The connector 19 is connected to the light source apparatus 21 of the peripheral apparatus 10. Various kinds of mouthpieces and various kinds of electrical contacts which are not shown in the drawings are provided in the connector 19. The video processor 22 is also electrically connected to the connector 19 via the connection cable 23. Note that the configuration of the endoscope apparatus 1 described above is merely one example, and the present invention is not limited to the above described configuration.

Figure 2:
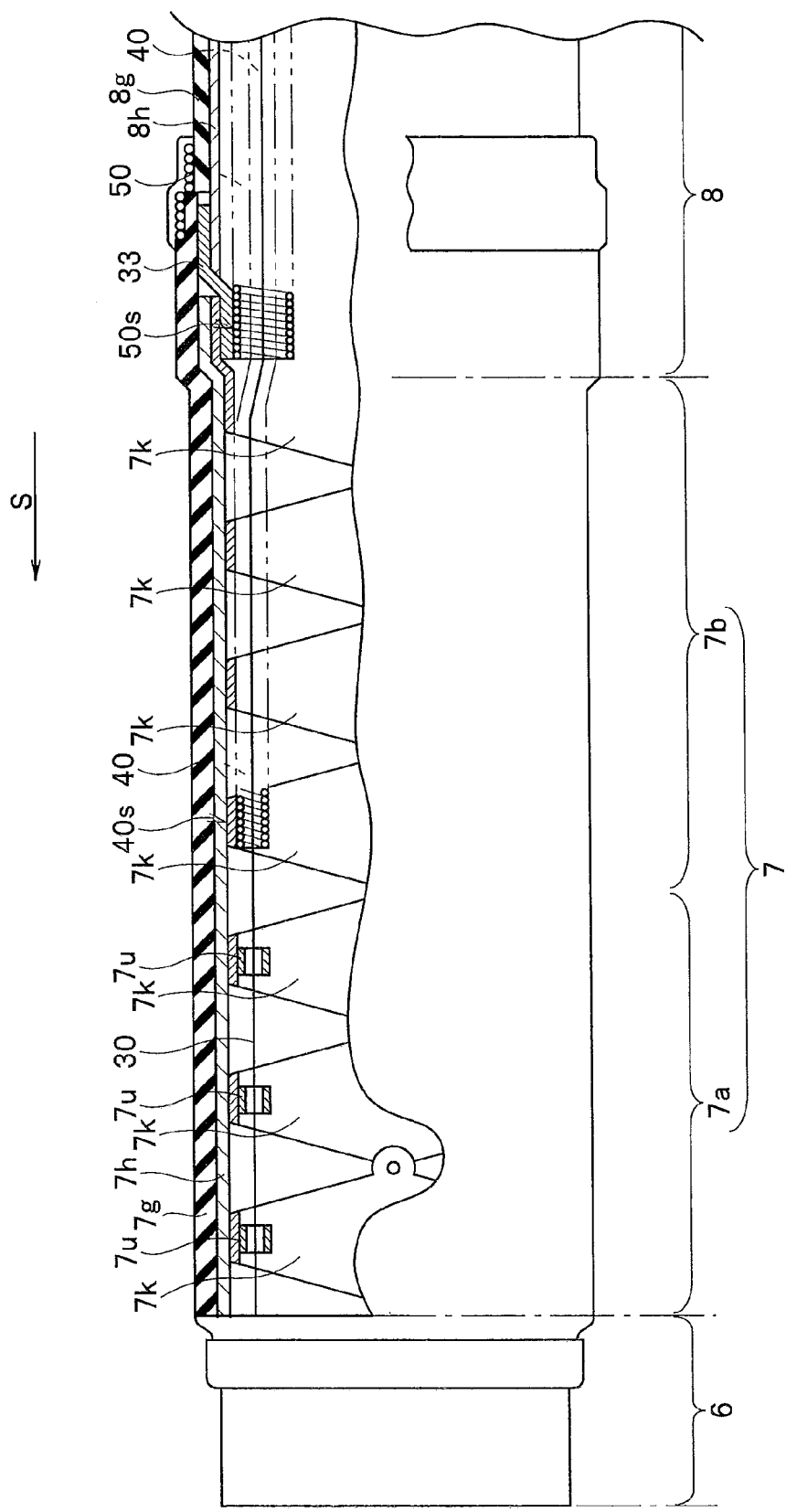
FIG. 2 is a partial cross-sectional view that schematically illustrates an internal configuration of a distal end side of an insertion portion shown in FIG. 1 according to the first embodiment of the present invention.
Figure 3:
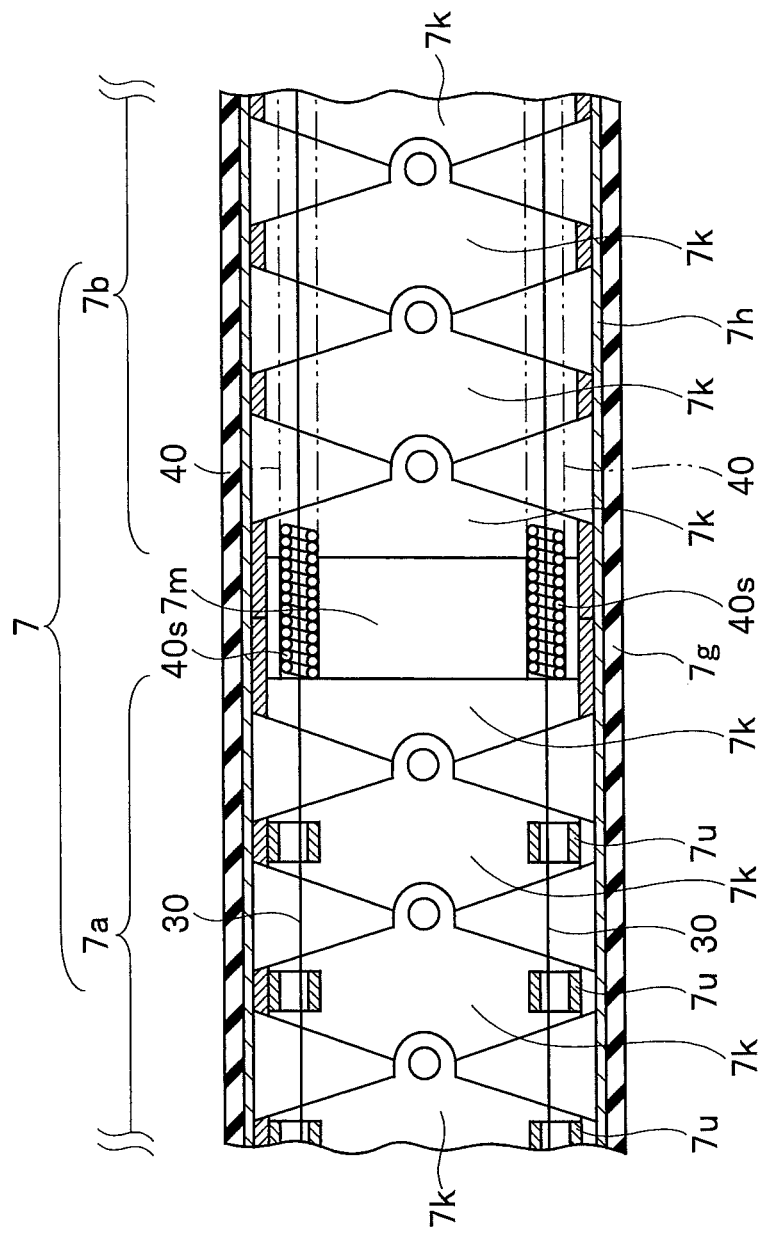
FIG. 3 is a partial cross-sectional view that illustrates a modification in which a first region and a second region of a bending portion shown in FIG. 2 are connected by a connecting mouthpiece according to the first embodiment of the present invention.

Next, the internal configuration of the distal end side of the insertion portion 4 will be described using FIG. 2 and FIG. 3. FIG. 2 is a partial cross-sectional view that schematically illustrates the internal configuration of the distal end side of the insertion portion shown in FIG. 1. FIG. 3 is a partial cross-sectional view that illustrates a modification in which a first region and a second region of a bending portion shown in FIG. 2 are connected by a connecting mouthpiece.

As shown in FIG. 2, a plurality of bending pieces 7k are provided in a linked manner along the insertion direction S inside the bending portion 7. The outer circumferences of the plurality of bending pieces 7k are covered with a braid 7h, and the outer circumference of the braid 7h is covered with a bending rubber 7g.

Note that hereunder, a region located in a front half portion in the insertion direction S in the bending portion 7 is referred to as a "first region 7a", and a region located in a rear half portion in the insertion direction S in the bending portion 7 is referred to as a "second region 7b".

Inside the operation portion 3 and the insertion portion 4 are provided, for example, four wires 30 that are inserted through the operation portion 3 and the insertion portion 4 at positions that are staggered from each other by approximately 90° in the circumferential direction of the insertion portion 4. The four wires 30 are movable forward and rearward in the insertion direction S (hereunder, referred to simply as "forward and rearward"), and vary the operating state of the bending portion 7, that is, cause the bending portion 7 to bend. Further, wire guides 7u that hold the four wires 30 are respectively provided in the plurality of bending pieces 7k located in the first region 7a inside the operation portion 3 and the insertion portion 4.

The distal ends of the respective wires 30 are fixed to the bending piece 7k located at the farthest position on the distal end side in the insertion direction S among the plurality of bending pieces 7k.

Figure 4:
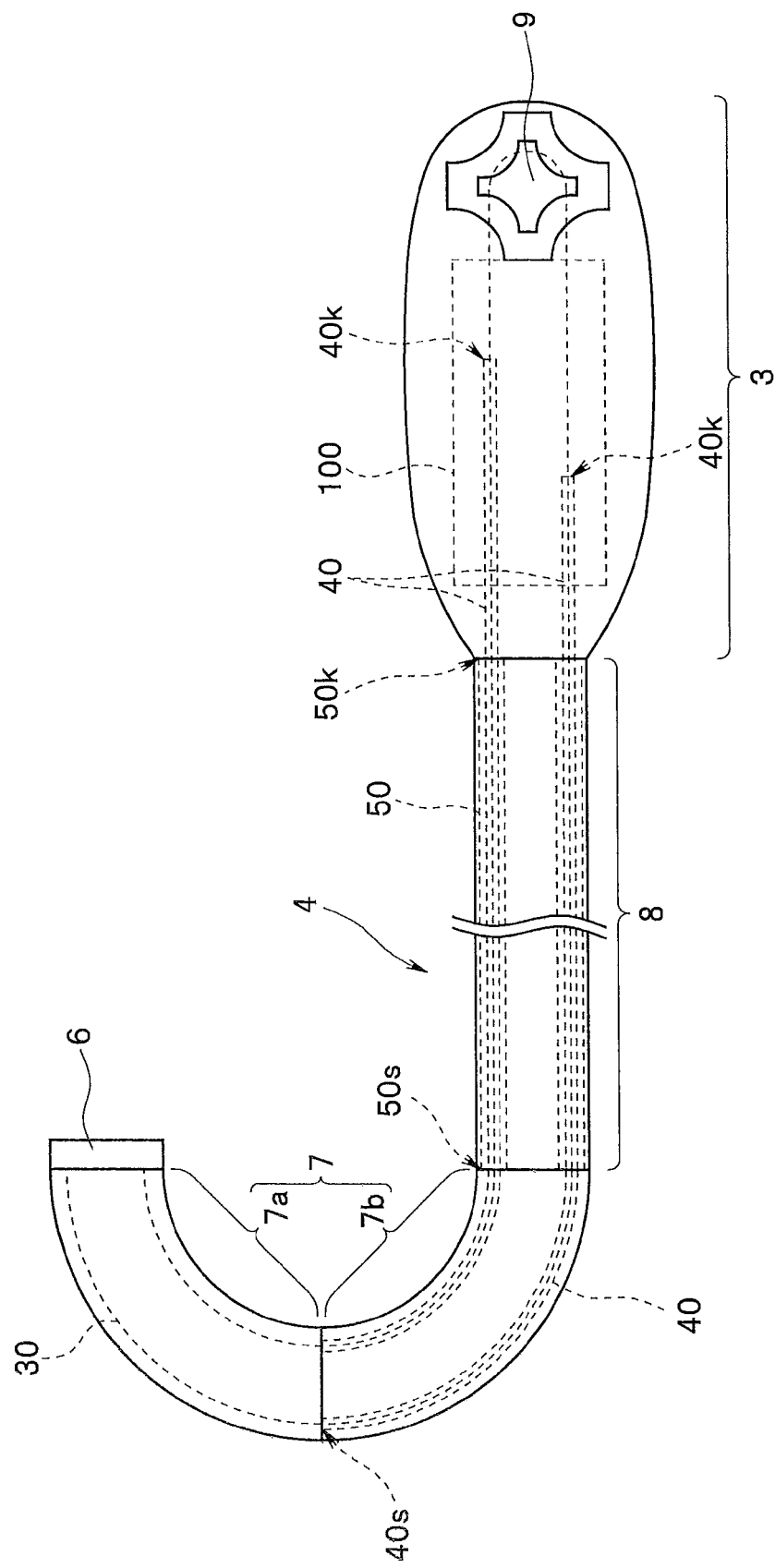
FIG. 4 is a view that schematically illustrates a state in which, with respect to the bending portion shown in FIG. 2, the bending portion is bent from a proximal end side of the second region according to the first embodiment of the present invention.

As shown in FIG. 4 that is described later, the respective proximal ends of two of the wires 30 for upward and downward bending are wound around a sprocket that is not shown in the drawings that is connected to the upward/downward bending operation knob 9a of the bending operation knobs 9. Further, the respective proximal ends of two of the wires 30 for left and right bending are wound around a sprocket that is not shown in the drawings that is connected to the leftward/rightward bending operation knob 9b and that is different to the sprocket connected to the upward/downward bending operation knob 9a of the bending operation knobs 9.

That is, when the upward/downward bending operation knob 9a is operated, one of the two wires 30 for upward and downward bending is moved rearward in the insertion direction S (hereunder, referred to simply as "rearward") and the other of the two wires 30 for upward and downward bending is moved forward in the insertion direction S (hereunder, referred to simply as "forward"). That is, the bending portion 7 bends in either one of the upward and downward directions as the result of one wire of the two wires 30 for upward and downward bending being pulled and the other wire being relaxed.

Further, when the leftward/rightward bending operation knob 9b is operated, one of the two wires 30 for left and right bending is moved rearward and the other is moved forward. That is, the bending portion 7 bends in either one of the right and left directions as the result of one wire of the two wires 30 for left and right bending being pulled and the other wire being relaxed.

In the second region 7b, a distal end side of a connecting member 33 is fixed to the bending piece 7k located at the farthest position on the proximal end side among the plurality of bending pieces 7k. A distal end side of a braid 8h that is included in the flexible tube portion 8 is fixed to the outer circumference of the proximal end side of the connecting member 33. Note that the outer circumference of the braid 8h is covered by a covering tube 8g.

The outer circumferences of the four wires 30 that are inserted through the inside of the operation portion 3 and the insertion portion 4 are respectively covered by an inner guide sheath 40 that is a linear member that can vary a bending state of the bending portion. The inner guide sheath 40 is constituted by, for example, a flexible coil pipe that is elongated along the insertion direction S.

That is, four of the inner guide sheaths 40 are inserted through the inside of the operation portion 3 and the insertion portion 4 at staggered positions in the circumferential direction of the insertion portion 4. Note that, each inner guide sheath 40 is formed from, for example, a coil pipe made of stainless steel.

Further, the respective wires 30 are arranged so as to be movable forward and rearward inside the respective inner guide sheaths 40.

The reason each of the inner guide sheaths 40 is constituted by a flexible coil pipe is that, for example, if the outer circumference of each wire 30 is covered by an ordinary rigid pipe made of metal, not only the bending portion 7 will no longer bend, but furthermore the flexibility of the flexible tube portion 8 will decrease.

Hence, a member constituting the respective inner guide sheaths 40 is not limited to a coil pipe as long as the member does not reduce the bendability of the bending portion 7 and the flexibility of the flexible tube portion 8, and can resist a compressive force that acts along an extension direction of each inner guide sheath 40 when the bending portion 7 bends.

Further, as shown in FIG. 2, a distal end 40s of each inner guide sheath 40 is fixed by, for example, brazing to the braid 7h at a midway position, for example, a distal end position of the second region 7b, in the insertion direction S of the bending portion 7.

Note that a proximal end 40k of each inner guide sheath 40 is configured to be switchable between a fixed state and a non-fixed state by a linear member fixing mechanism 100 that is described later (see FIG. 4) that is provided inside the operation portion 3. That is, the linear member fixing mechanism 100 is a mechanism for fixing the movement in the insertion direction S of each inner guide sheath 40. Note that the linear member fixing mechanism 100 is described later.

Furthermore, as shown in FIG. 2, the outer circumferences of the four inner guide sheaths 40 located inside the flexible tube portion 8 are respectively covered by outer guide sheaths 50 constituted by, for example, a flexible coil pipe. Note that each of the inner guide sheaths 40 that are inserted through the inside of the respective outer guide sheaths 50 are configured to freely advance and retract in the insertion direction S. The respective outer guide sheaths 50 are also formed from, for example, a coil pipe made of stainless steel.

The respective outer guide sheaths 50 need not cover the outer circumferences of all four of the inner guide sheaths 40. For example, a configuration may be adopted in which the outer guide sheath 50 covers only the outer circumference of the inner guide sheath 40 that covers the outer circumference of the wire 30 that causes the bending portion 7 to bend in the upward direction. In such a case, it is sufficient that the distal end 40s and the proximal end 40k of each of the three inner guide sheaths 40 that are not covered by the outer guide sheath 50 are fixed.

Note that because the flexibility of the flexible tube portion 8 will decrease if the wires 30 are doubly covered by a coil sheath used in the conventional product, the thickness and material of the conventional coil sheath as well as the cross-sectional shape of an element wire thereof are adapted to form a flexible coil sheath so that both the inner and outer coil sheaths can withstand a pulling force of the wires 30 and do not buckle under a compressive force that bends the bending portion 7 and so that the flexibility of the flexible tube portion 8 does not significantly decrease even when the wires 30 are doubly covered.

Hence, a member constituting the respective outer guide sheaths 50 is not limited to a coil pipe as long as the member does not reduce the flexibility of the flexible tube portion 8 and can resist a compressive force that acts along an extension direction of each outer guide sheath 50 when the bending portion 7 bends.

In addition, as shown in FIG. 2, a distal end 50s of each outer guide sheath 50 is fixed by, for example, brazing to the distal end of the flexible tube portion 8, more specifically, to the proximal end side of the connecting member 33. Further, a proximal end 50k of each outer guide sheath 50 is fixed by, for example, brazing to a stopper member 90 (see FIG. 7) at a position that is more rearward than the flexible tube portion 8.

Because the respective outer guide sheaths 50 are inserted through the flexible tube portion 8 in a state in which the distal end 50s and the proximal end 50k (see FIG. 7) of each outer guide sheath 50 are fixed in this manner, when any one of the four wires 30 is pulled to bend the bending portion 7, each outer guide sheath 50 resists a compressive force that acts on the flexible tube portion 8 along an extension direction of the outer guide sheath 50. Thus, the occurrence of a situation in which the flexible tube portion 8 that has flexibility bends together with the bending portion 7 is prevented.

Note that, each inner guide sheath 40 is formed along the insertion direction S to a length such that, in a state in which the distal end 50s and the proximal end 50k of each outer guide sheath are fixed, the distal ends 40s of the respective inner guide sheaths 40 are fixed to the distal end of the second region 7b and the proximal ends 40k of the respective inner guide sheaths 40 are not drawn further to the distal end side than the proximal ends 50k of the respective outer guide sheaths 50.

Further, as shown in FIG. 3, the bending portion 7 may have a configuration in which the first region 7a and the second region 7b are connected along the insertion direction S by a connecting mouthpiece 7m.

More specifically, the bending portion 7 may have a configuration in which the first region 7a and the second region 7b are connected through the connecting mouthpiece 7m by fitting a bending piece 7k that is located at a position that is furthest on the proximal end side in the first region 7a and a bending piece 7k that is located at a position that is furthest on the distal end side in the second region 7b to the connecting mouthpiece 7m that has an outer diameter that is smaller than an inner diameter of the respective bending pieces 7k.

Note that a hole that is not illustrated in the drawings is formed in the bending piece 7k located at the position that is furthest on the proximal end side in the first region 7a and the bending piece 7k located at the position that is furthest on the distal end side in the second region 7b, respectively, and the respective pieces 7k are fastened with a screw or the like that is not illustrated in the drawings that is screwed into a threaded screw hole that is not illustrated in the drawings that is provided in the connecting mouthpiece 7m via the aforementioned holes.

In the configuration illustrated in FIG. 3, the distal ends 40s of the four inner guide sheaths 40 are fixed by, for example, brazing to the connecting mouthpiece 7m.

According to the configuration shown in FIG. 3, in comparison to the configuration in FIG. 2, the assemblability is improved since it is sufficient to join the distal ends 40s of the respective inner guide sheaths 40 to the connecting mouthpiece 7m when joining the distal ends 40s to a midway position of the bending portion 7.

Figure 5:
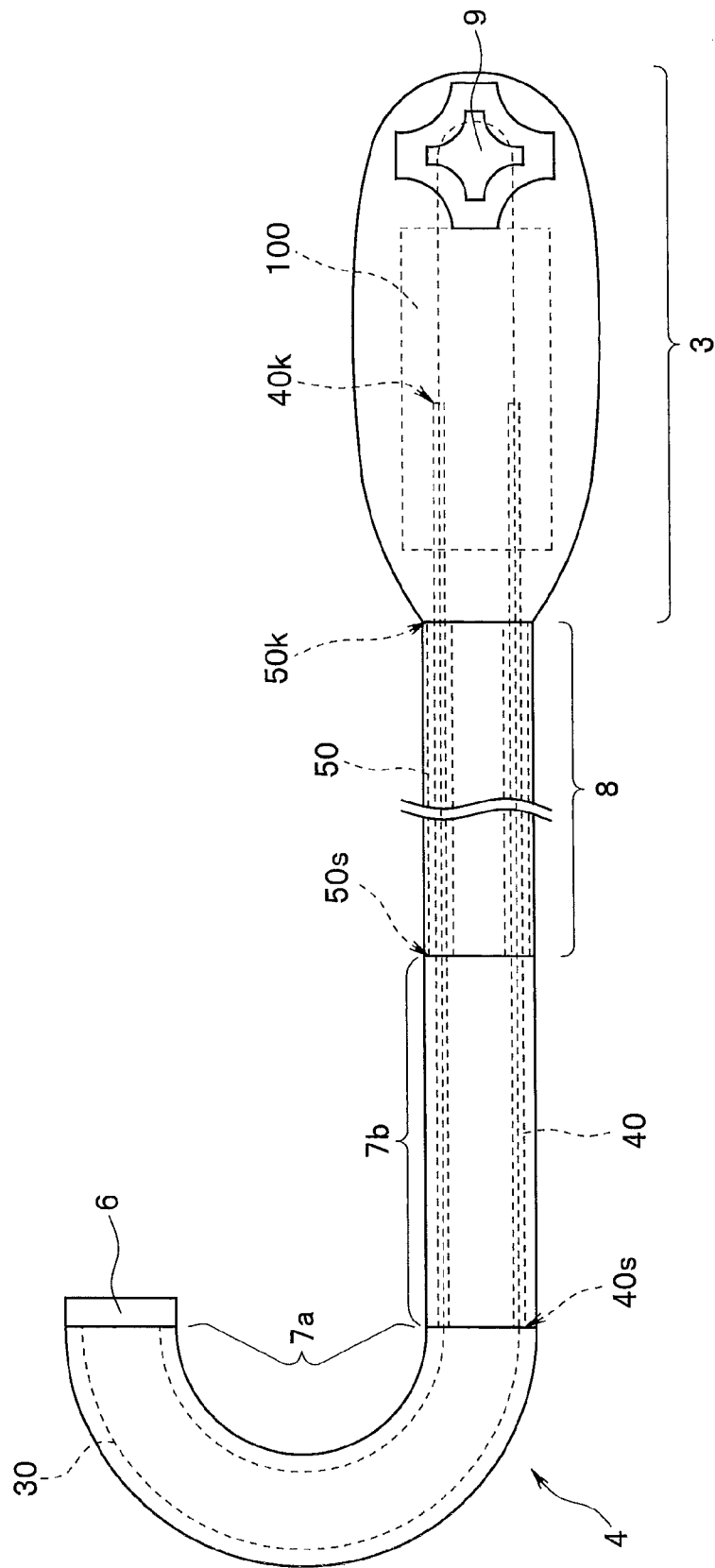
FIG. 5 is a view that schematically illustrates a state in which, with respect to the bending portion shown in FIG. 2, the bending portion is bent from a proximal end side of the first region according to the first embodiment of the present invention.
Figure 6:
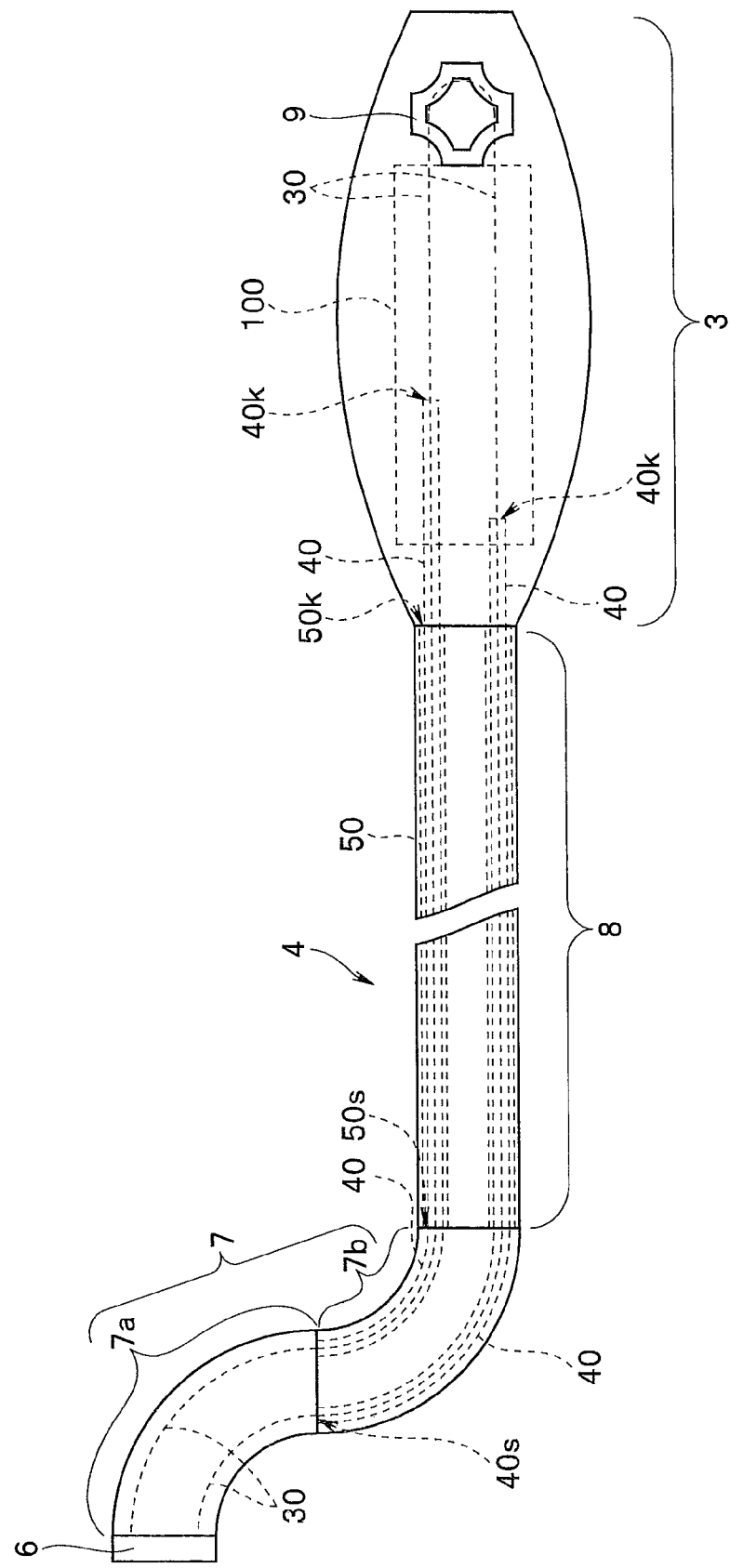
FIG. 6 is a view that schematically illustrates a state in which the proximal end of the inner guide sheath shown in FIG. 4 is fixed, and the first region of the bending portion shown in FIG. 4 is bent to an opposite side to the bending direction of the second region according to the first embodiment of the present invention.

Next, a bending operation of the bending portion shown in FIG. 2 is described using FIG. 4 to FIG. 6. FIG. 4 is a view that schematically illustrates a state in which, with respect to the bending portion shown in FIG. 2, the bending portion is bent from a proximal end side of the second region. FIG. 5 is a view that schematically illustrates a state in which, with respect to the bending portion shown in FIG. 2, the bending portion is bent from a proximal end side of the first region. FIG. 6 is a view that schematically illustrates a state in which the proximal end of the inner guide sheath shown in FIG. 4 is fixed, and the first region of the bending portion shown in FIG. 4 is bent to an opposite side to the bending direction of the second region.

First, if an operator wishes to bend the bending portion 7 from the proximal end side of the second region 7b, that is, if the operator wishes to bend the entire bending portion 7, without performing an operation to rotate the fixing lever 80, the operator releases the fixed state of the proximal ends 40k of the respective inner guide sheaths 40 that were fixed using the linear member fixing mechanism 100.

In this state, when the operator operates one of the upward/downward bending operation knob 9a and the leftward/rightward bending operation knob 9b among the bending operation knobs 9 to pull any wire 30 among the four wires 30, because the proximal ends 40k are not fixed, the respective inner guide sheaths 40 cannot resist a compressive force that acts along the extension direction of the respective inner guide sheaths 40 in the second region 7b of the bending portion 7, and consequently the proximal ends 40k move rearward.

Further, because the distal ends 50s and proximal ends 50k of the respective outer guide sheaths 50 are fixed inside the flexible tube portion 8, the respective outer guide sheaths 50 resist a compressive force that acts along the extension direction of the respective outer guide sheaths 50.

As a result, as shown in FIG. 4, the first region 7a and the second region 7b of the bending portion 7 bend from the proximal end side of the second region 7b in a manner that takes the distal ends of the respective outer guide sheaths 50 as a starting point. More specifically, the entire bending portion 7 bends.

Next, if the operator wishes to bend only the first region 7a of the bending portion 7, the operator rotationally operates the fixing lever 80 to fix the proximal ends 40k of the respective inner guide sheaths 40 using the linear member fixing mechanism 100.

In this state, when the operator operates one of the upward/downward bending operation knob 9a and the leftward/rightward bending operation knob 9b among the bending operation knobs 9 to pull any wire 30 among the four wires 30, because the proximal ends 40k are fixed, the respective inner guide sheaths 40 resist a compressive force that acts along the extension direction of the respective inner guide sheaths 40 in the second region 7b of the bending portion 7.

As a result, as shown in FIG. 5, in the bending portion 7, only the first region 7a bends from the proximal end side of the first region 7a in a manner that takes the distal ends of the respective inner guide sheaths 40 as a starting point.

Further, as shown in FIG. 4, when the proximal ends 40k of the respective inner guide sheaths 40 are in a non-fixed state, if the upward/downward bending operation knob 9a is operated to pull any one of the four wires 30, for example, the wire 30 on the upper side, the first region 7a and the second region 7b bend upward as described above. Thereafter, if the operator wishes to bend the first region 7a in a different direction to the second region 7b, the operator rotationally operates the fixing lever 80 to fix the proximal ends 40k of the respective inner guide sheaths 40 by means of the linear member fixing mechanism 100.

Thereafter, when the operator operates the upward/downward bending operation knob 9a to pull the wire 30 on the lower side, as shown in FIG. 6, because the proximal ends 40k are fixed, in a state in which the second region 7b is fixed in an upward bending shape, only the first region 7a bends downward in the opposite direction to the upward direction from the proximal end side thereof.

Note that the bending directions are not limited to the upward and downward directions. That is, in a state in which the second region 7b is bending upward, the first region 7a may be bent to the left or right by pulling the respectively corresponding wire 30. Furthermore, in a state in which the second region 7b is bending to any one of the upward, downward, left, and right sides, the first region 7a may be bent to any one of the upward, downward, left and right sides that is different to the bending direction of the second region 7b.

That is, the endoscope 2 of the present embodiment has a configuration in which the first region 7a and the second region 7b can be bent in different directions to each other. Note that because the first region 7a and the second region 7b can be bent in different directions to each other, an effect can be anticipated that facilitates observation and treatment at a place at which it is difficult to view a lesion from the front, such as the gastric cardia, the vicinity of the back of the anus in the rectum, and the back of a fold of the colon. Furthermore, the present configuration allows a surgeon to simply perform a bending operation using only one hand.

Thus, the bending state of the bending portion 7 can be switched by switching between a fixed state and a non-fixed state with respect to the proximal ends 40k of the respective inner guide sheaths 40.

Figure 7:
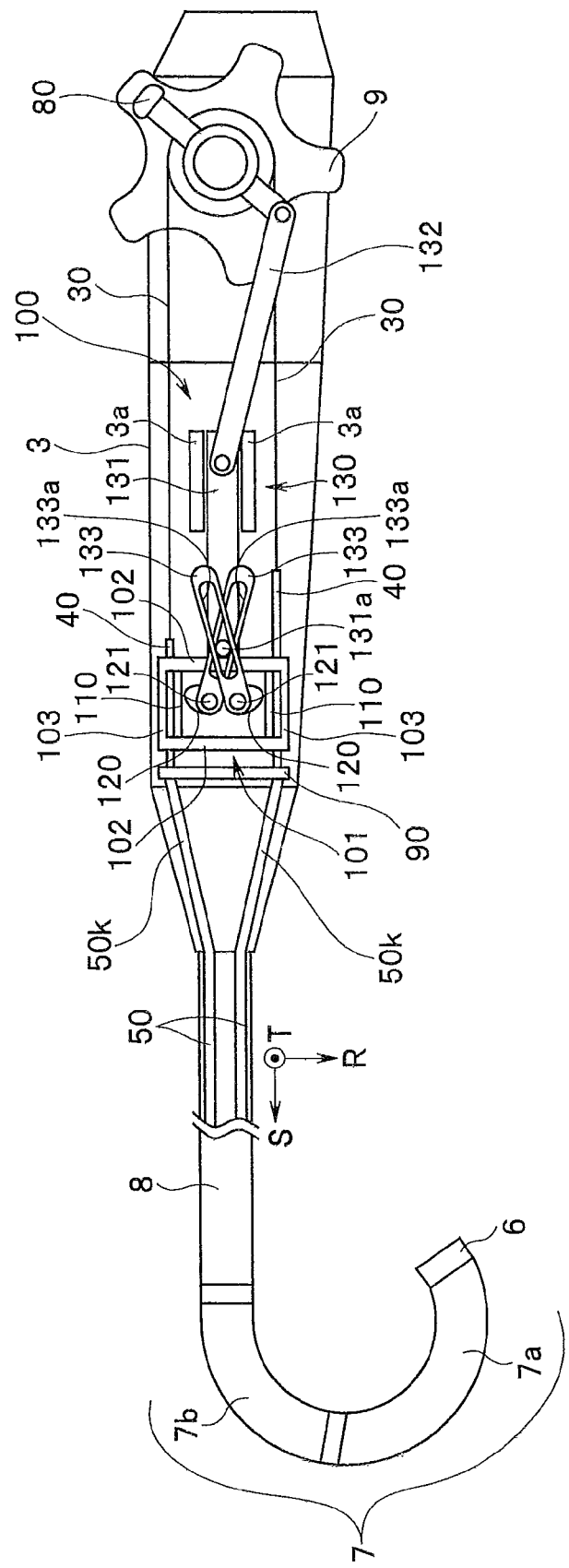
FIG. 7 is a schematic configuration diagram that illustrates, together with the insertion portion and the operation portion, a linear member fixing mechanism provided inside the operation portion of the endoscope according to the first embodiment of the present invention, which is a view showing a state in which inner guide sheaths are placed in a non-fixed state by the linear member fixing mechanism.
Figure 8:
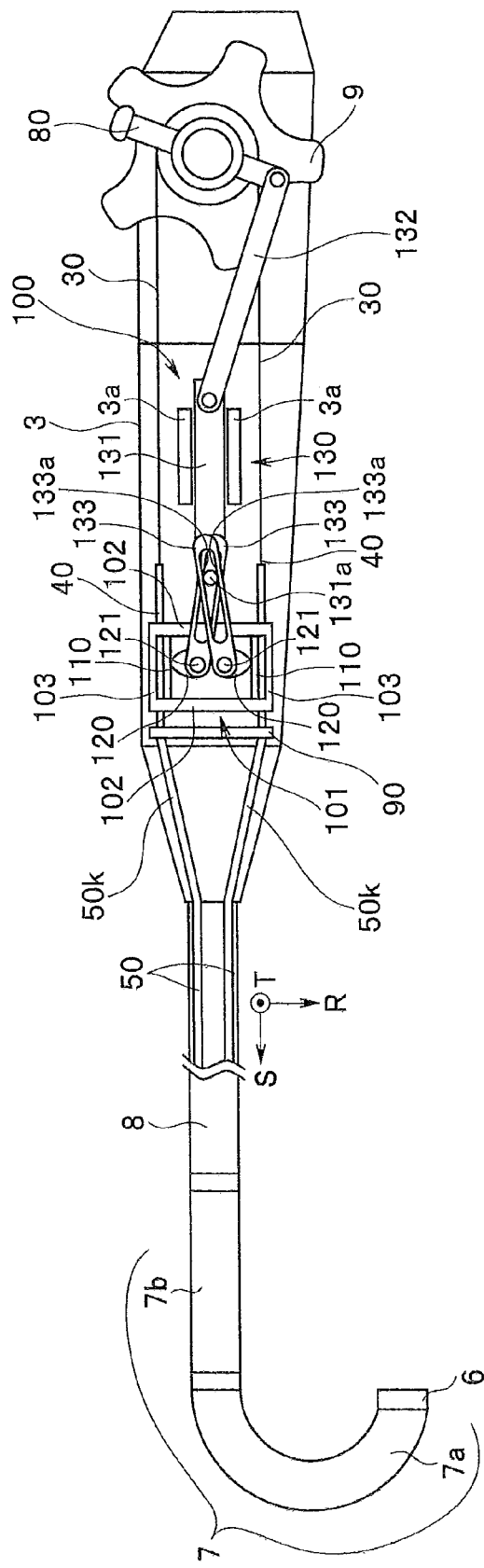
FIG. 8 is a schematic configuration diagram that illustrates, together with the insertion portion and the operation portion, the linear member fixing mechanism provided inside the operation portion of the endoscope according to the first embodiment of the present invention, which is a view showing a state in which inner guide sheaths are placed in a fixed state by the linear member fixing mechanism.
Figure 9:
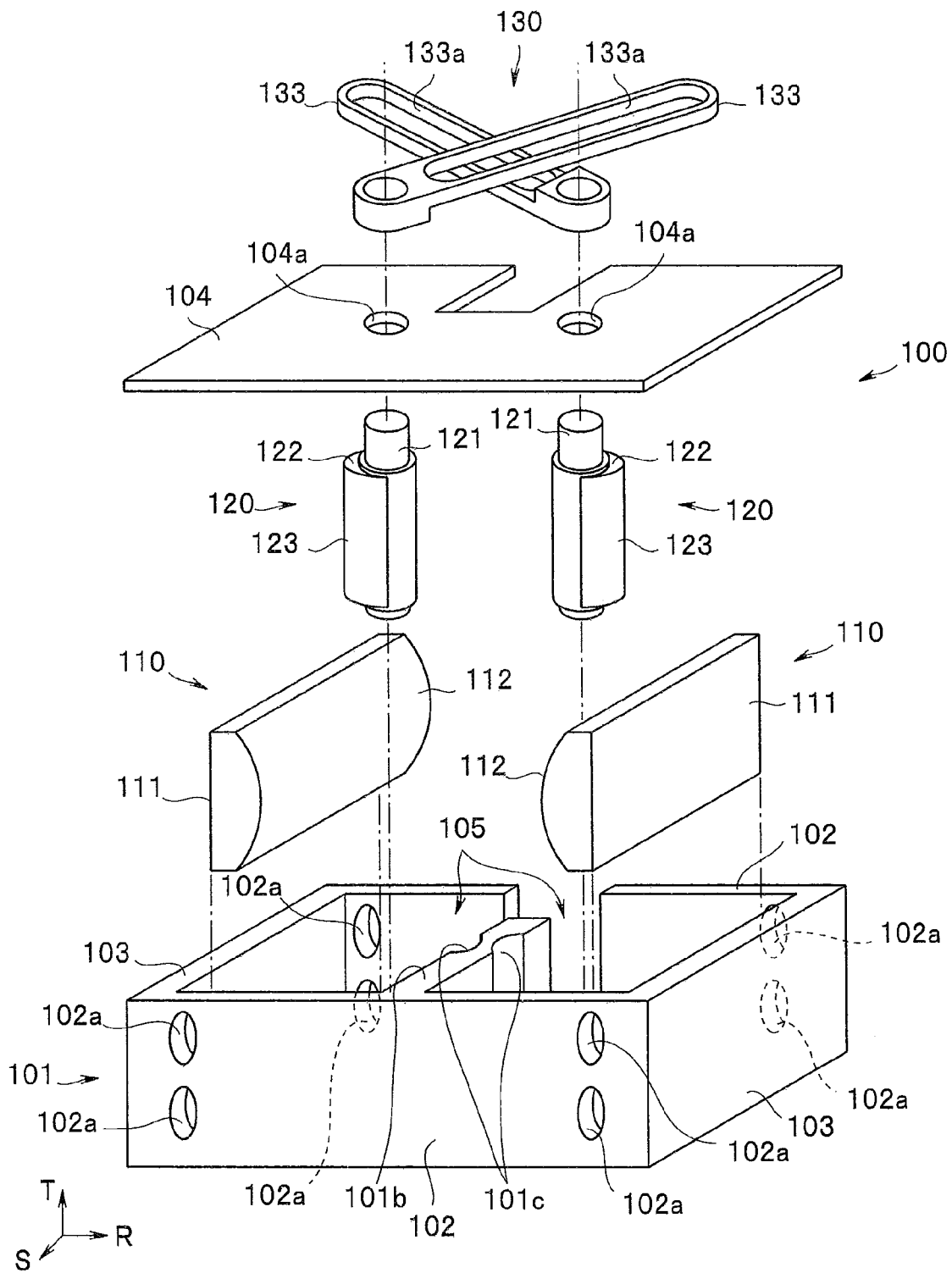
FIG. 9 is an exploded perspective view illustrating main parts of the linear member fixing mechanism according to the first embodiment of the present invention.
Figure 10:
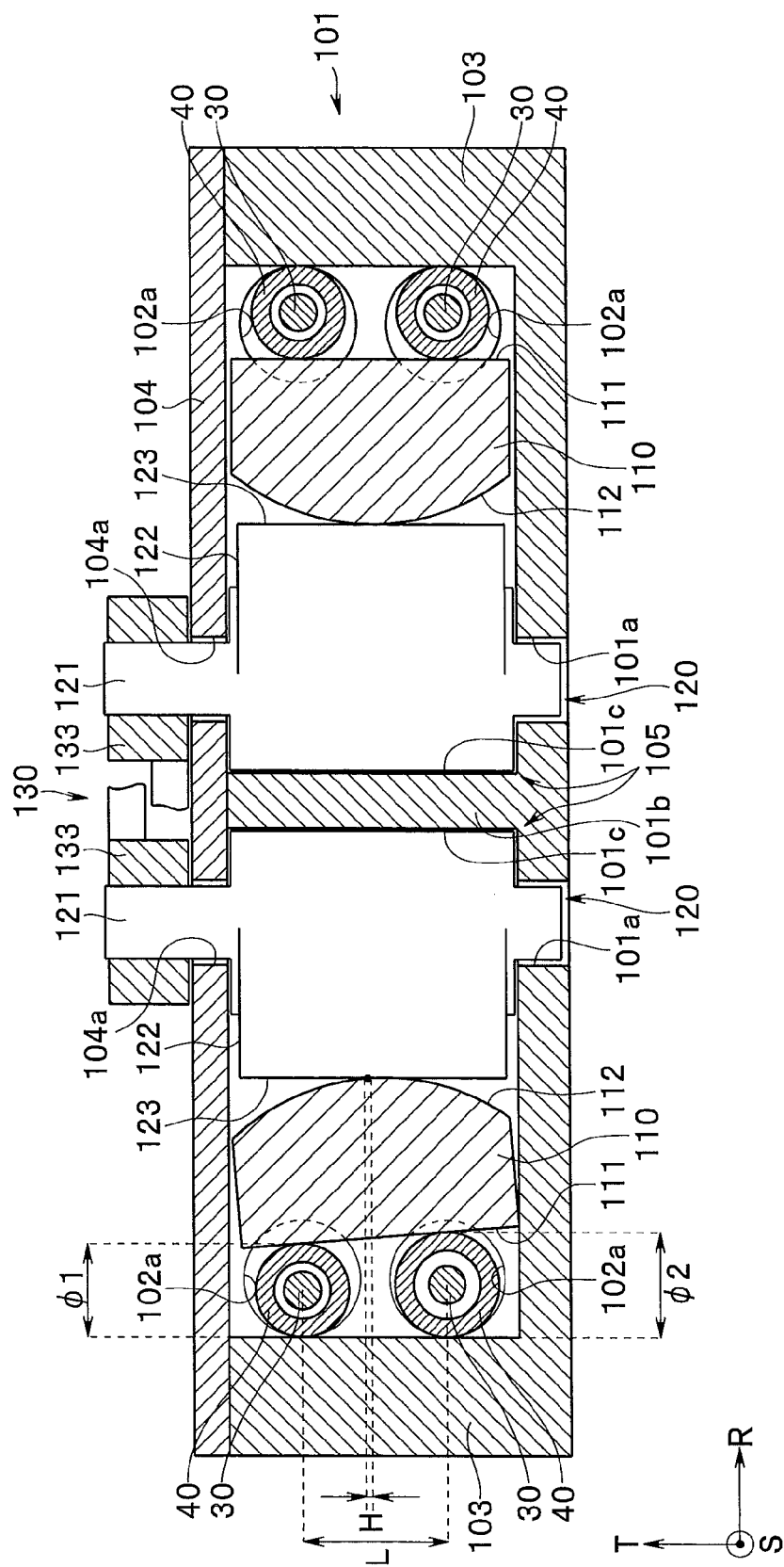
FIG. 10 is a cross-sectional view of main parts of the linear member fixing mechanism according to the first embodiment of the present invention.

Next, the linear member fixing mechanism 100 that fixes the proximal ends 40k of the respective inner guide sheaths 40 that are linear members is described using FIG. 7 to FIG. 10. FIG. 7 is a schematic configuration diagram that illustrates, together with the insertion portion and the operation portion, the linear member fixing mechanism provided inside the operation portion of the endoscope, which is a view showing a state in which the inner guide sheaths are placed in a non-fixed state by the linear member fixing mechanism. FIG. 8 is a schematic configuration diagram that illustrates, together with the insertion portion and the operation portion, the linear member fixing mechanism provided inside the operation portion of the endoscope, which is a view showing a state in which the inner guide sheaths are placed in a fixed state by the linear member fixing mechanism. FIG. 9 is an exploded perspective view illustrating main parts of the linear member fixing mechanism. FIG. 10 is a cross-sectional view of main parts of the linear member fixing mechanism.

As shown in FIG. 7 to FIG. 10, the linear member fixing mechanism 100 that simultaneously prohibits (fixes) movement in the insertion direction S on the proximal end 40k side of the four inner guide sheaths 40 is provided inside the operation portion 3.

The linear member fixing mechanism 100 includes a guide frame 101 through which the four inner guide sheaths 40 are inserted, a pair of braking members 110 that are housed inside the guide frame 101, a pair of eccentric cams 120 as pressing members for contacting against each of the braking members 110, respectively, in a manner in which the eccentric cams 120 are capable of contacting with and separating from the respective braking members 110 inside the guide frame 101, and a link mechanism 130 that causes the respective eccentric cams 120 to move in response to an operation of the fixing lever 80.

As shown in FIGS. 9 and 10, the guide frame 101 is constituted by a bottomed frame body formed in the shape of a flat, approximately rectangular cylinder. A bottom portion of the guide frame 101 is fixed inside the operation portion 3 (see FIGS. 7 and 8), for example, by a screw clamp or the like that is not illustrated in the drawings. By fixing the bottom portion in this manner, among four side wall portions of the guide frame 101, first side wall portions 102 that form one pair of side wall portions extend in a direction R that is perpendicular to the longitudinal axis direction S of the insertion portion 4, and second side wall portions 103 that form the other pair of side wall portions extend in the longitudinal axis direction S of the insertion portion 4.

As shown in FIG. 9, two through-holes 102*a* are formed in each of the two end portions (two end portions in the direction R that is perpendicular to the longitudinal axis direction S) of the respective first side wall portions 102 in the vicinity of the respective second side wall portions 103 (that is, in each of the first side wall portions 102, four through-holes 102*a* are respectively formed which face each other). The through-holes 102*a* are holes that are used to support each of the four inner guide sheaths 40. Individual inner guide sheaths 40 are respectively inserted into each pair of through-holes 102*a* that face each other in the first side wall portions 102 in a state in which play exists between the relevant inner guide sheath 40 and the corresponding through-holes 102*a* (see FIG. 10). Thus, the guide frame 101 supports the four inner guide sheaths 40 in a manner in which respective pairs of the inner guide sheaths 40 are supported in a parallel condition along an inner wall face of each second side wall portion 103, and allows advancing and retracting movement in the longitudinal axis direction S of the respective inner guide sheaths 40.

In addition, as shown in FIG. 9, inside the guide frame 101, a partition wall portion 101*b* that extends in the longitudinal axis direction S of the insertion portion 4 is arranged in a standing condition, and bearing grooves 101*c* corresponding to camshafts 121 of the eccentric cams 120 that are described later are provided in the two side faces of the partition wall portion 101*b*. Further, as shown in FIG. 10, a lid body 104 is provided over an opening portion of a top portion of the guide frame 101. The lid body 104 is fixed to the guide frame 101 by a screw clamp or the like that is not illustrated in the drawings to thereby form a pair of brake chambers 105 that form a hollow for housing the braking members 110 and the eccentric cams 120, respectively, between the guide frame 101 and the lid body 104.

Each braking member 110 is constituted by a plate-like member that extends inside the brake chamber 105 along the longitudinal axis direction S. Each of the braking members 110 faces an inner wall face of each of the second side wall portions 103, respectively, through two inner guide sheaths 40 that are adjacent, and are configured to be movable in the direction R that is approximately perpendicular to the side wall portions 103. That is, the respective braking members 110 are arranged inside the brake chamber 105 in a state in which the respective braking members 110 are movable in the direction R that is approximately perpendicular to the movement direction (longitudinal axis direction S) of two inner guide sheath 40 interposed between each braking member 110 and the corresponding second side wall portion 103 and also to the interaxial direction T.

In the respective braking members 110, faces that are opposite the second side wall portions 103 are respectively set as contact faces 111 having an area capable of coming in contact with two inner guide sheaths 40 simultaneously. On the other hand, in the respective braking members 110, a rear face of each contact face 111 is provided as a face to be pressed 112 that can be pressed by the eccentric cam 120.

As shown in FIGS. 9 and 10, each eccentric cam 120 is configured to have a camshaft 121 that is pivotably supported between bearing holes 101*a* and 104*a* that are formed in the bottom portion of the guide frame 101 and the lid body 104, respectively, and a cam member 122 that protrudes in an eccentric condition in a direction perpendicular to the axis of the camshaft 121. Here, as shown in FIG. 10, when pivotally supported between the bearing holes 101*a* and 104*a*, the camshaft 121 is brought into sliding contact with the bearing groove 101*c* formed in the partition wall portion 101*b* of the guide frame 101. As a result, a deformation of the camshaft 121 can be suppressed and wear of the bearing holes 101*a* and 104*a* and the like can be reduced. Note that in the present embodiment the camshaft 121 and the cam member 122 are constituted by an integrally molded component.

A cam face 123 is formed as a pressing face on a circumferential face of each cam member 122. The cam face 123 is configured to be capable of contacting the face to be pressed 112 of the braking member 110 in a manner in which the cam face 123 is capable of contacting with and separating from the face to be pressed 112 accompanying rotation of the camshaft 121. At a time of contact with the face to be pressed 112, the cam member 122 presses the braking member 110 with a pressing force in accordance with the rotational state of the camshaft 121.

In this case, as shown in FIGS. 9 and 10, the face to be pressed 112 of each braking member 110 is constituted by a convex curved face that bends along the interaxial direction T of two inner guide sheaths 40 and has a top portion between the axes of the two inner guide sheaths 40. Note that although an example in which the face to be pressed 112 is constituted by an arcuate face is shown in FIGS. 9 and 10, the shape of the convex curved face is not limited thereto, and for example, may be an arbitrary convex curved face having a single top portion such as a parabolic cylindrical face.

In contrast, the cam face 123 of each cam member 122 is constituted by a flat face along the interaxial direction T of the two inner guide sheaths 40.

By constituting the face to be pressed 112 of each braking member 110 with the above described convex curved face, as shown in FIG. 10, contact between the face to be pressed 112 and the cam face 123 in the interaxial direction T of the two inner guide sheaths 40 is set so that a contact width H thereof is shorter than an interaxial distance L between the two inner guide sheaths 40 and also so that the contact position is located between the axes of the two inner guide sheaths 40.

As shown in FIGS. 7 and 8, the link mechanism 130 is configured to have a slider 131 arranged inside the operation portion 3, a connecting arm 132 that connects the slider 131 and the fixing lever 80, and a pair of cam levers 133 that connect the slider 131 and the respective eccentric cams 120.

The slider 131 is constituted, for example, by a long plate-like member. The slider 131 is, for example, disposed between a pair of guide walls 3*a* provided in a standing condition inside the operation portion 3, so that the slider 131 can advance and retract along the longitudinal axis direction S inside the operation portion 3.

One end portion of the connecting arm 132 is pivotably supported by an end portion of the fixing lever 80, and the other end portion of the connecting arm 132 is pivotably supported by a proximal end portion of the slider 131, so that the connecting arm 132 thereby connects the fixing lever 80 and the slider 131. By means of this connection through the connecting arm 132, a rotational motion of the fixing lever 80 is converted to an advancing/retracting movement (rectilinear advancing movement) of the slider 131.

Each cam lever 133 is constituted by a long plate-like member in which a long hole 133*a* is formed. A fixed end portion of each of the cam levers 133 is installed in a fixed condition at the camshafts 121 of the eccentric cams 120, respectively, and a free end side of each cam lever 133 is disposed inside the operation portion 3 in a state in which the free end sides intersect with each other. A slider pin 131*a* that is provided in a standing condition at a distal end portion of the slider 131 is inserted through the two long holes 133*a* that are superimposed on each other as a result of the intersection of the respective cam levers 133. A rectilinear advancing movement of the slider 131 is converted to a rotational movement of each eccentric cam 120 by means of the connection via the cam levers 133.

In the linear member fixing mechanism 100 configured as described above, for example, as shown in FIG. 7, when the fixing lever 80 is rotationally operated in the counter-clockwise direction in the drawing, the connecting arm 132 pushes the slider 131 outward in the longitudinal axis direction S to cause the slider 131 to advance towards the distal end side inside the operation portion 3. Accompanying this advancing movement, an engagement position of the slider pin 131a in each long hole 133a moves to the fixed end side of the respective cam levers 133 (that is, the distal end side of the operation portion 3). As a result, the respective cam levers 133 shift in a direction that widens an angle formed by the two cam levers 133. In response to the shifting of the cam levers 133, the respective eccentric cams 120 rotate in a direction that causes the respective cam faces 123 to come in contact with the faces to be pressed 112 of the respective braking members 110 and thereby press the braking members 110. As a result, the contact face 111 of each braking member 110 contacts against the respective inner guide sheaths 40 with a predetermined pressing force, and each of the braking members 110 holds two inner guide sheaths 40, respectively, in an immobilized state between the respective braking members 110 and the respective second side wall portions 103. Note that, in the link mechanism 130 of the present embodiment, the length of each cam lever 133 is set to a sufficiently long length, and a distance from the camshaft 121 to the engagement position between the long hole 133a and the slider pin 131a is set to be sufficiently longer than a protruding length of the cam member 122 based on the camshaft 121 so that it is thereby possible to boost an operating force with respect to the fixing lever 80 by a predetermined amount and convert the operating force to a pressing force of the cam member 122.

In this case, by setting the contact between the face to be pressed 112 and the cam face 123 in the interaxial direction T of the two inner guide sheaths 40 so that the contact width H thereof is shorter than the interaxial distance L and so that the contact position is located between the axes of two inner guide sheaths 40, for example, even in a case where, as shown on the left side in FIG. 10, external diameters φ1 and φ2 of the two inner guide sheaths 40 forming a pair are slightly different from each other, the braking member 110 can be tilted to cause the contact face 111 thereof to simultaneously contact against the respective inner guide sheaths 40, and a pressing force from the eccentric cam 120 can be transmitted equally to the respective inner guide sheaths 40. Naturally, for example, as shown on the right side in FIG. 10, in a case where the external diameters of two inner guide sheaths 40 are approximately equal also, the contact face 111 of the braking member 110 can be caused to simultaneously contact against the respective inner guide sheaths 40.

In contrast, for example, as shown in FIG. 8, when the fixing lever 80 is rotationally operated in the clockwise direction, the connecting arm 132 pulls the slider 131 in the longitudinal axis direction S to cause the slider 131 to withdraw to the proximal end side inside the operation portion 3. Accompanying this withdrawal movement, the engagement position of the slider pin 131a in the respective long holes 133a moves to the free end side of each cam lever 133 (that is, the proximal end side of the operation portion 3). As a result, the respective cam levers 133 shift in a direction that makes an angle formed by the cam levers 133 a narrow angle. In response to the shifting of the cam levers 133, the respective eccentric cams 120 rotate in a direction that causes the respective cam faces 123 to separate from the faces to be pressed 112 of the respective braking members 110. As a result, the respective inner guide sheaths 40 are released from the contact faces 111 of the respective braking members 110, thus allowing movement in the longitudinal axis direction S of the respective inner guide sheaths 40.

According to the embodiment described above, even when there is a slight difference between the external diameters of the respective inner guide sheaths 40, one-sided contact of the contact face 111 with respect to the respective inner guide sheaths 40 can be prevented. Accordingly, simultaneous fixing of the respective inner guide sheaths 40 can be accurately performed with even a small amount of operating force, and without an excessive amount of operating force being applied to the fixing lever 80. Further, since it is not necessary to impart an excessive amount of operating force to the fixing lever 80, it is possible to reduce the size of the linear member fixing mechanism 100 and improve the durability thereof, and also reduce a burden on an operator and the like.

Note that although in the above described embodiment an example has been described in which the face to be pressed 112 is constituted by a convex curved face that bends along the interaxial direction T and the cam face 123 is constituted by a flat face along the interaxial direction T, a configuration may also be adopted in which, for example, the face to be pressed 112 is constituted by a flat face along the interaxial direction T and the cam face 123 is constituted by a convex curved face that bends along the interaxial direction T.

Figure 11:
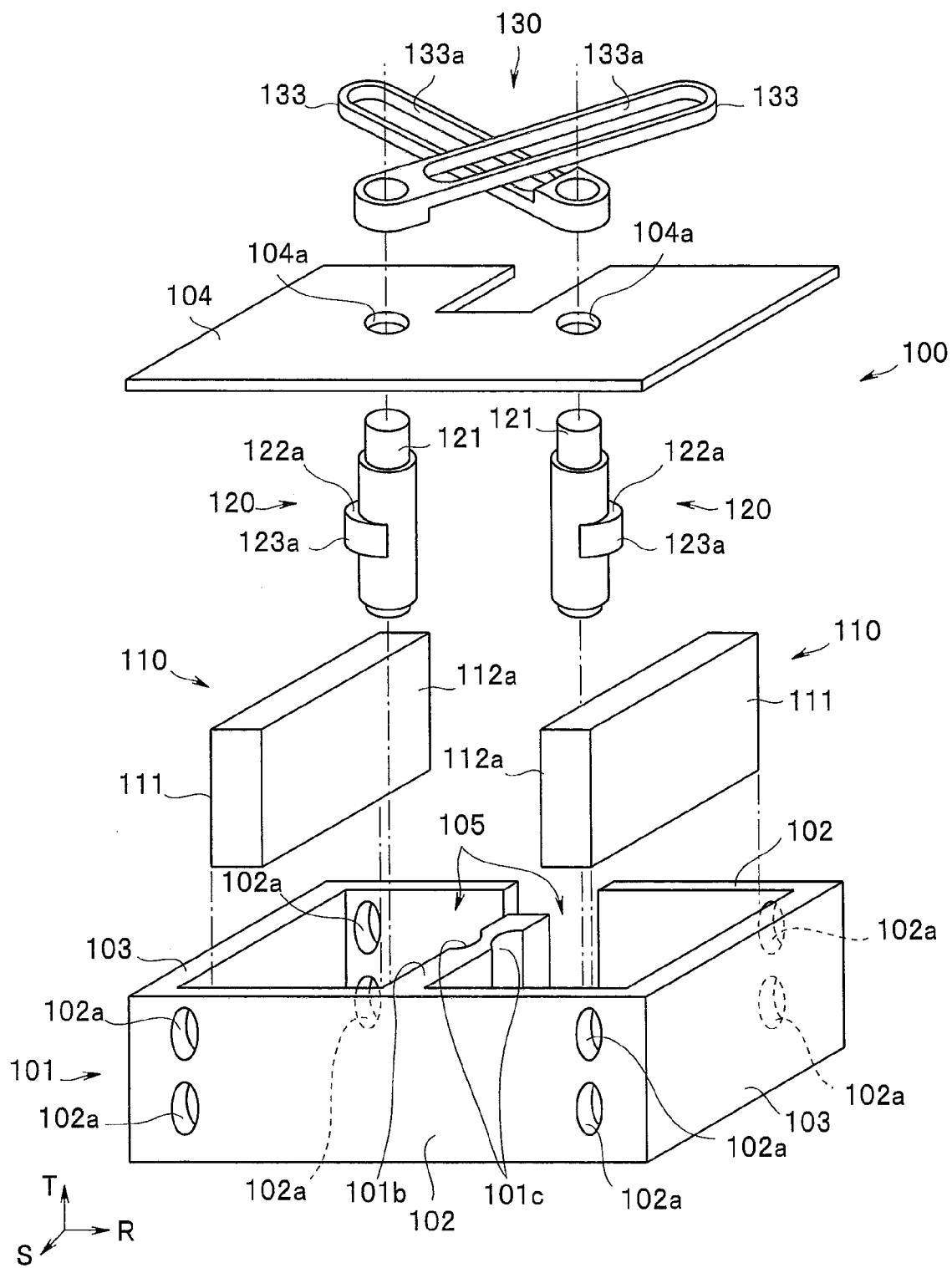
FIG. 11 is an exploded perspective view illustrating main parts of a linear member fixing mechanism according to a second embodiment of the present invention.
Figure 12:
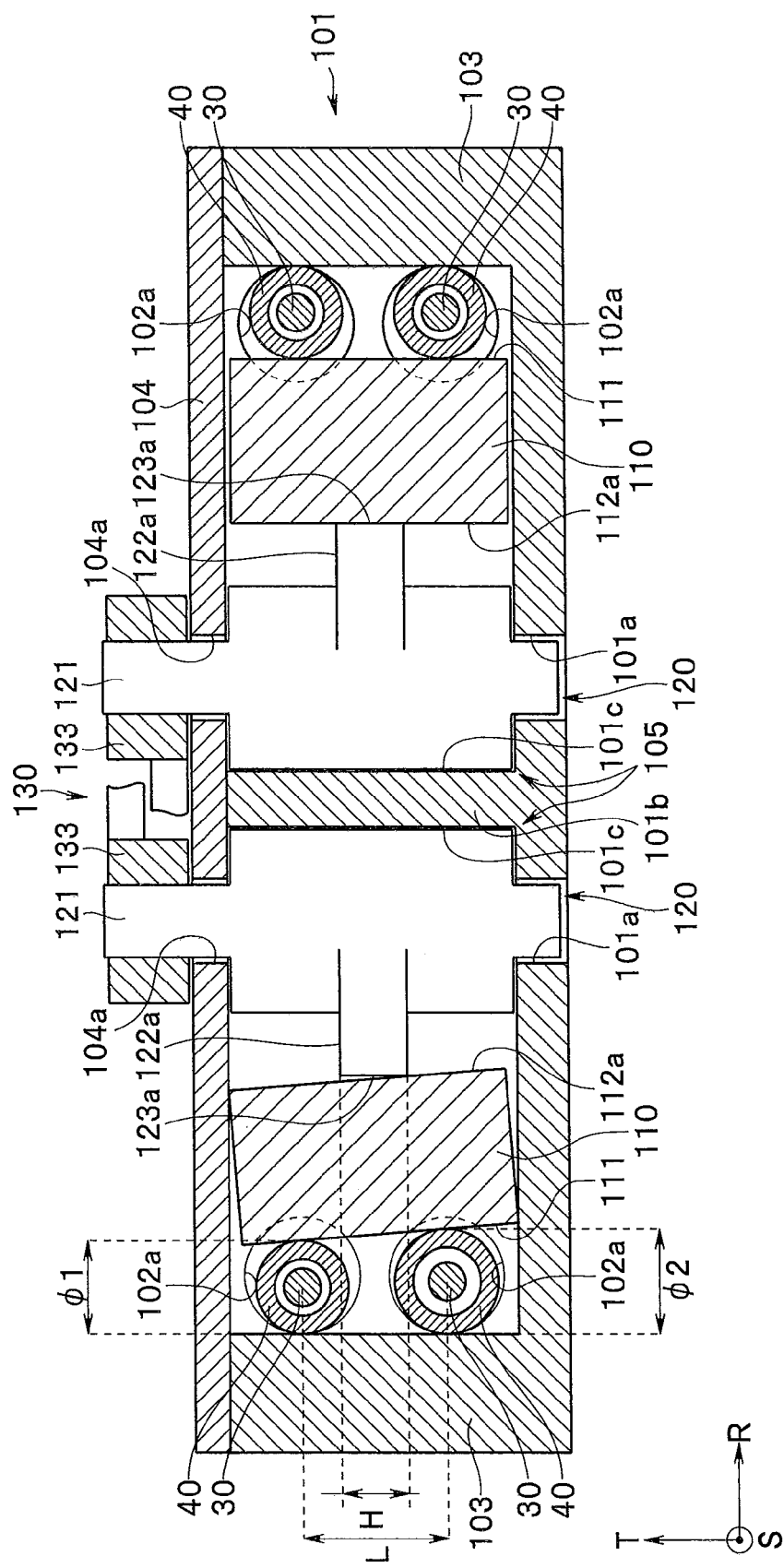
FIG. 12 is a cross-sectional view of main parts of the linear member fixing mechanism according to the second embodiment of the present invention.

FIGS. 11 and 12 relate to a second embodiment of the present invention. FIG. 11 is an exploded perspective view illustrating main parts of the linear member fixing mechanism. FIG. 12 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 11 and 12, faces to be pressed 112a and cam faces 123a as pressing faces are each configured as flat faces along the interaxial direction T of two of the inner guide sheaths 40.

However, a cam member 122a of the present embodiment is constituted by a thin plate-like member (convex portion). Consequently, a width in the interaxial direction T of the cam face 123a is set so as to be shorter than the interaxial distance L between two inner guide sheaths 40.

By constituting the cam member 122a with a thin plate-like member, as shown in FIG. 12, contact between the face to be pressed 112a and the cam face 123a in the interaxial direction T of two of the inner guide sheaths 40 is set so that the contact width H thereof is shorter than the interaxial distance L between the two inner guide sheaths 40 and also so that the contact position is located between the axis of the two inner guide sheaths 40.

According to this embodiment, in addition to the advantageous effects obtained by the above described first embodiment, an advantageous effect can also be obtained that the size of the linear member fixing mechanism 100 can be reduced in the width direction (direction R that is perpendicular to the longitudinal axis direction S) by an amount corresponding to an amount that is not required to form the convex curved face.

Note that, although an example in which a width in the interaxial direction T of the cam face 123a was shortened has been described in the above embodiment, for example, a configuration can also be adopted in which a convex strip (convex portion) is provided on the braking member 110, and a width in the interaxial direction T of the face to be pressed 112a can be shortened by setting the face to be pressed 112a on the convex portion.

Figure 13:
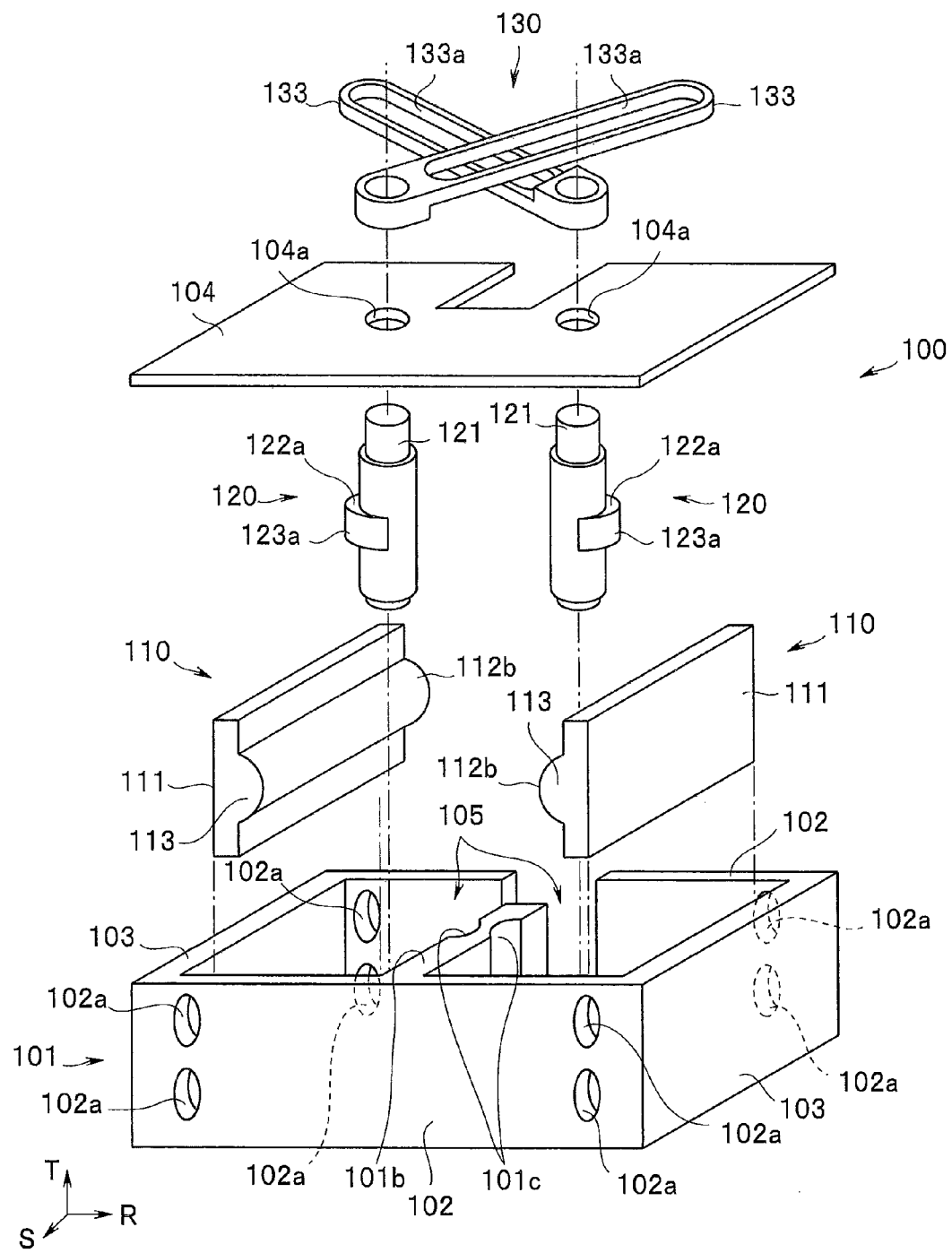
FIG. 13 is an exploded perspective view illustrating main parts of a linear member fixing mechanism according to a third embodiment of the present invention.
Figure 14:
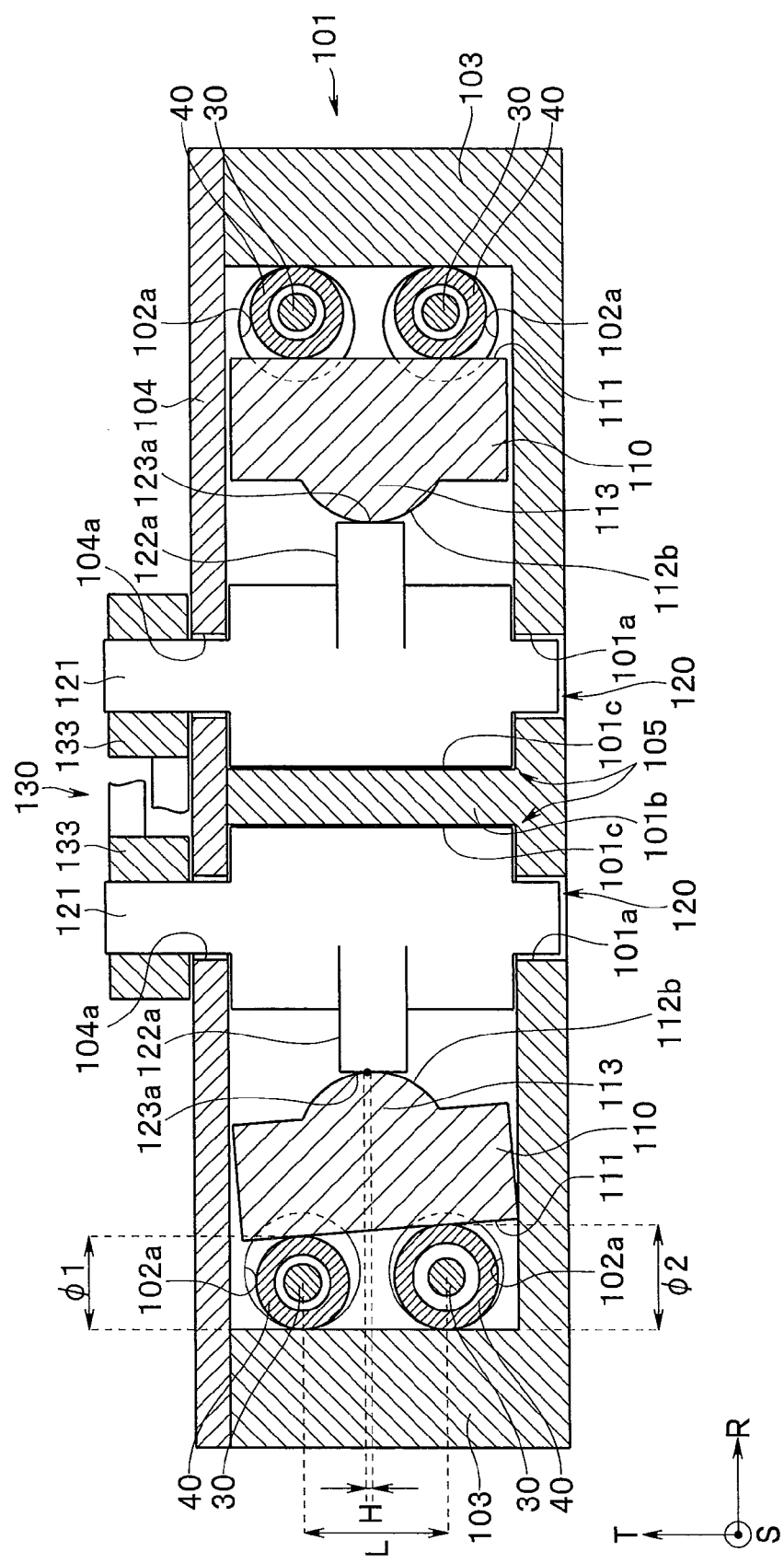
FIG. 14 is a cross-sectional view of main parts of the linear member fixing mechanism according to the third embodiment of the present invention.

FIGS. 13 and 14 relate to a third embodiment of the present invention. FIG. 13 is an exploded perspective view illustrating main parts of the linear member fixing mechanism. FIG. 14 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 13 and 14, a convex strip 113 is provided on the rear face side of the contact face 111 in the braking member 110. A face to be pressed 112b that is constituted by a convex curved face that bends in the interaxial direction T is set on the convex strip 113.

On the other hand, the cam member 122a of the eccentric cam 120 is constituted by a thin plate-like member (convex portion), and therefore a width in the interaxial direction T of the cam face 123a as a pressing face is set so as to be shorter than the interaxial distance L between two of the inner guide sheaths 40.

Further, by constituting the face to be pressed 112b by means of a convex curved face that is provided on the convex strip 113 and constituting the cam member 122a by means of a thin plate-like member, as shown in FIG. 14, with respect to contact between the face to be pressed 112b and the cam face 123a in the interaxial direction T of two of the inner guide sheaths 40, the contact width H thereof is shorter than an interaxial distance L between the two inner guide sheaths 40 and the contact position is set so as to be located between the axes of the two inner guide sheaths 40.

According to this embodiment, substantially similar advantageous effects as those obtained according to the above described first embodiment can be obtained.

Note that although an example has been described in the foregoing embodiment in which the face to be pressed 112b is constituted by a convex curved face that bends along the interaxial direction T, and the cam face 123a is constituted by a flat face along the interaxial direction T, for example, a configuration can also be adopted in which the face to be pressed 112b is constituted by a flat face along the interaxial direction T, and the cam face 123a is constituted by a convex curved face that bends along the interaxial direction T.

Figure 15:
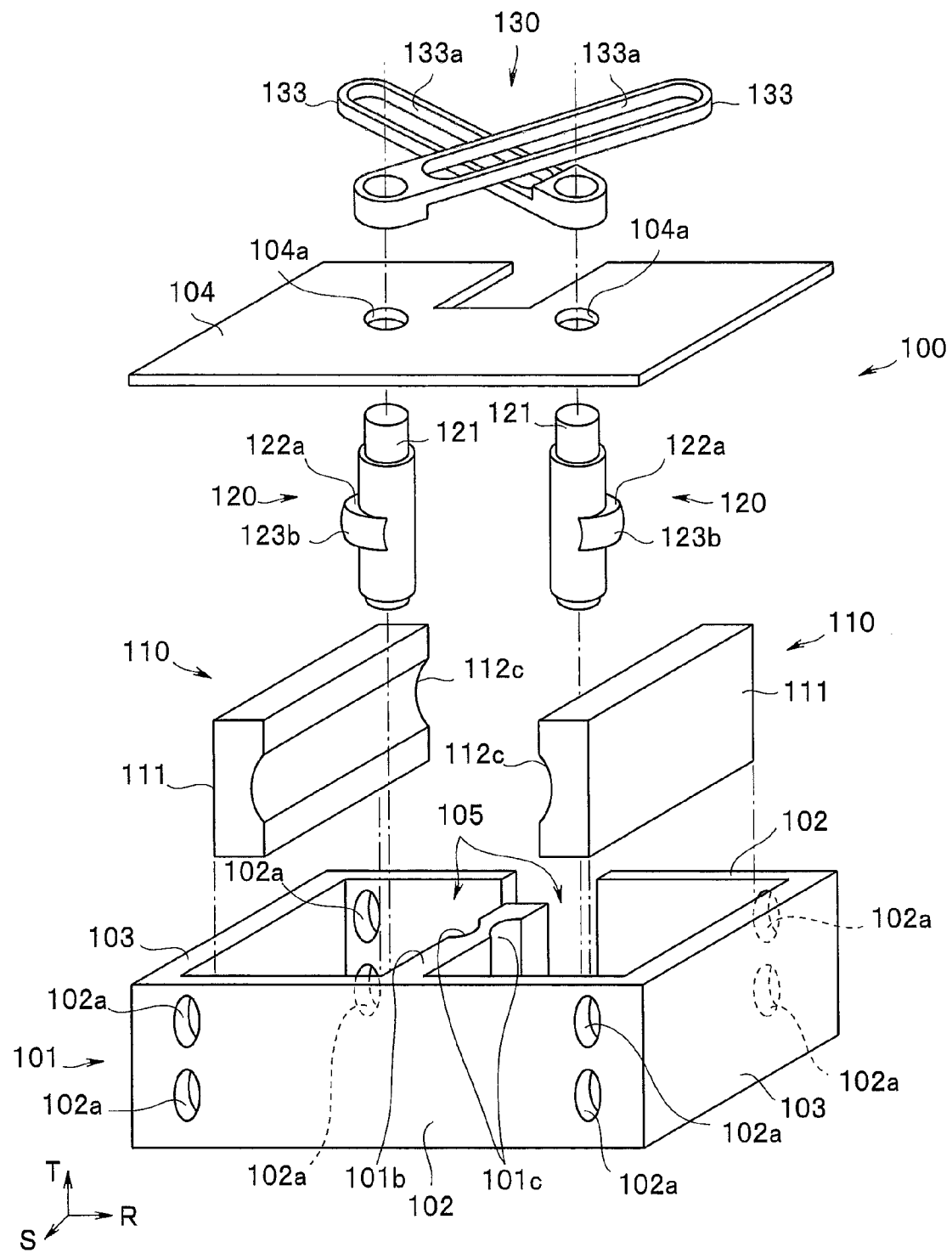
FIG. 15 is an exploded perspective view illustrating main parts of a linear member fixing mechanism according to a fourth embodiment of the present invention.
Figure 16:
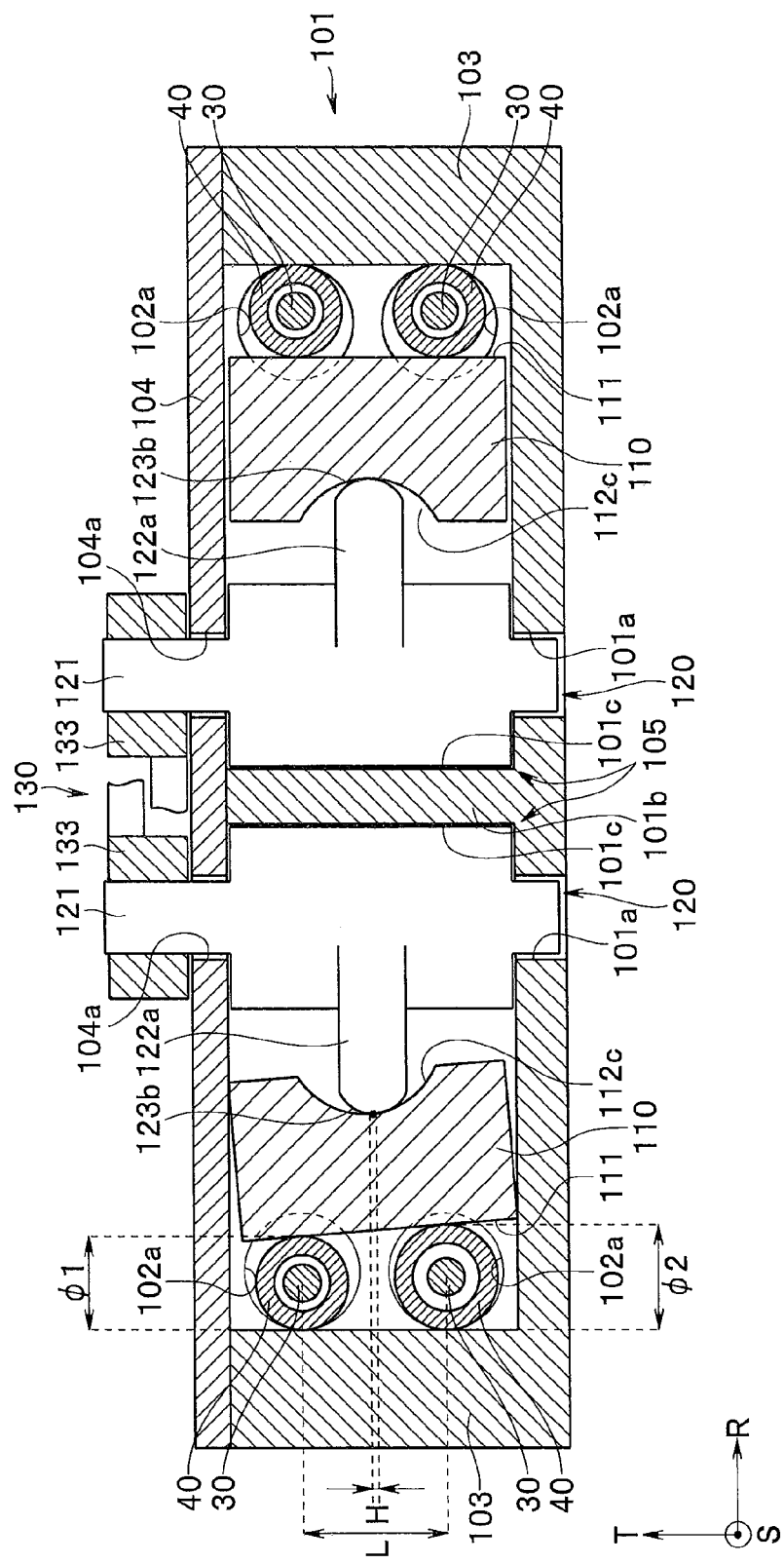
FIG. 16 is a cross-sectional view of main parts of the linear member fixing mechanism according to the fourth embodiment of the present invention.

FIGS. 15 and 16 relate to a fourth embodiment of the present invention. FIG. 15 is an exploded perspective view illustrating main parts of the linear member fixing mechanism. FIG. 16 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 15 and 16, a face to be pressed 112c formed of a concave curved face that bends along the interaxial direction T of two of the inner guide sheaths 40 and that has a bottom portion between the axes of the two inner guide sheaths 40 is set on a rear face side of the contact face 111 in the respective braking members 110.

The cam member 122a of the eccentric cam 120 is constituted by a thin plate-like member (convex portion). A cam face 123b of the cam member 122a is formed of a convex curved face that bends along the interaxial direction T of two of the inner guide sheaths 40 and has a top portion between the axes of the two inner guide sheaths 40.

By constituting the face to be pressed 112c by means of a concave curved face and constituting the cam face 123b by means of a convex curved face, as shown in FIG. 16, contact between the face to be pressed 112c and the cam face 123b in the interaxial direction T of the two inner guide sheaths 40 is set so that the contact width H thereof is shorter than the interaxial distance L between the two inner guide sheaths 40 and the contact position is located between the axes of the two inner guide sheaths 40.

According to this embodiment, in addition to the advantageous effects obtained by the foregoing first embodiment, by causing the concave curved face and the convex curved face to contact, an advantageous effect can also be obtained that the size of the linear member fixing mechanism 100 can be reduced in the width direction (direction R that is perpendicular to the longitudinal axis direction S).

Figure 17:
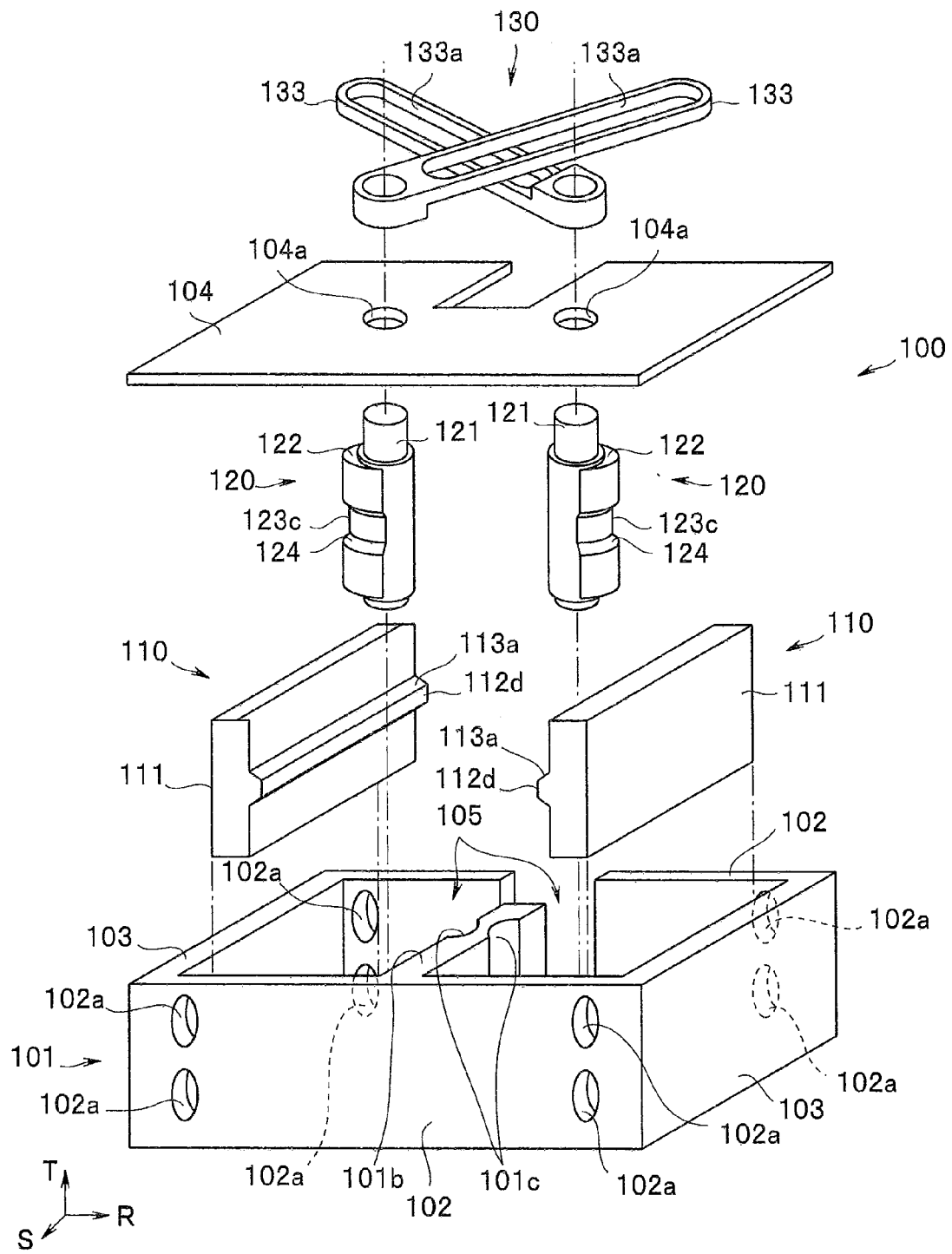
FIG. 17 is an exploded perspective view illustrating main parts of a linear member fixing mechanism according to a fifth embodiment of the present invention.
Figure 18:
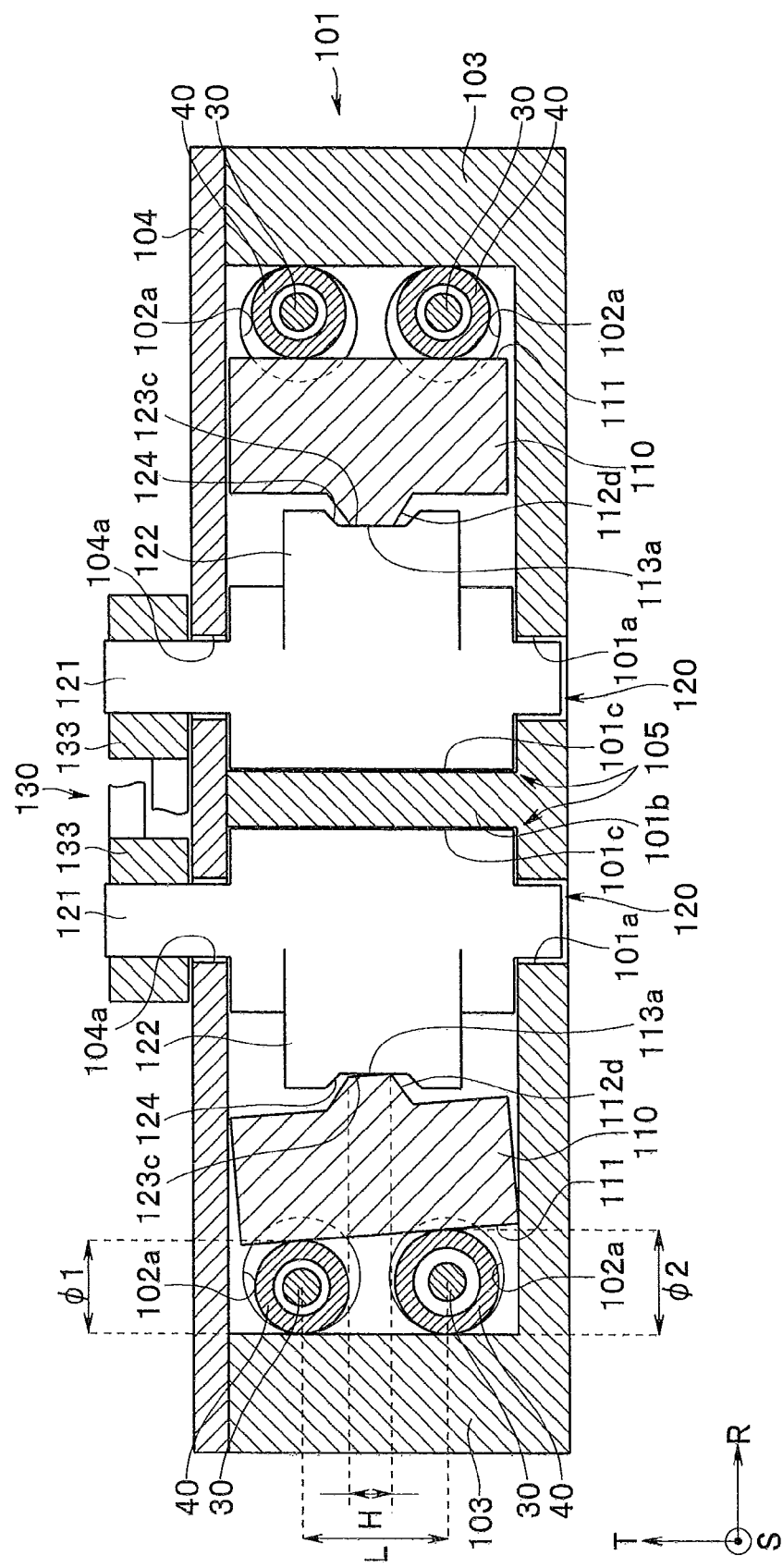
FIG. 18 is a cross-sectional view of main parts of the linear member fixing mechanism according to the fifth embodiment of the present invention.

FIGS. 17 and 18 relate to a fifth embodiment of the present invention. FIG. 17 is an exploded perspective view illustrating main parts of the linear member fixing mechanism. FIG. 18 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 17 and 18, a convex strip (convex portion) 113a is provided on a rear face side of the contact face 111 of each braking member 110, and a top face of the convex strip 113a is set as a face to be pressed 112d.

On the other hand, a concave groove (concave portion) 124 that corresponds to the convex strip 113a is provided on the cam member 122 of the eccentric cam 120. A bottom face of the concave groove 124 is set as a cam face 123c.

By setting the face to be pressed 112d on the convex strip 113a, and setting the cam face 123c in the concave groove 124, as shown in FIG. 18, contact between the face to be pressed 112d and the cam face 123c in the interaxial direction T of the two inner guide sheaths 40 is set so that the contact width H thereof is shorter than the interaxial distance L between the two inner guide sheaths 40 and the contact position is located between the axes of the two inner guide sheaths 40.

According to this embodiment, in addition to the advantageous effects obtained by the foregoing first embodiment, by causing the face to be pressed 112d that is set in the convex strip 113a and the cam face 123c that is set in the concave groove 124 to contact, an advantageous effect can also be obtained that the size of the linear member fixing mechanism 100 can be reduced in the width direction (direction R that is perpendicular to the longitudinal axis direction S).

Figure 19:
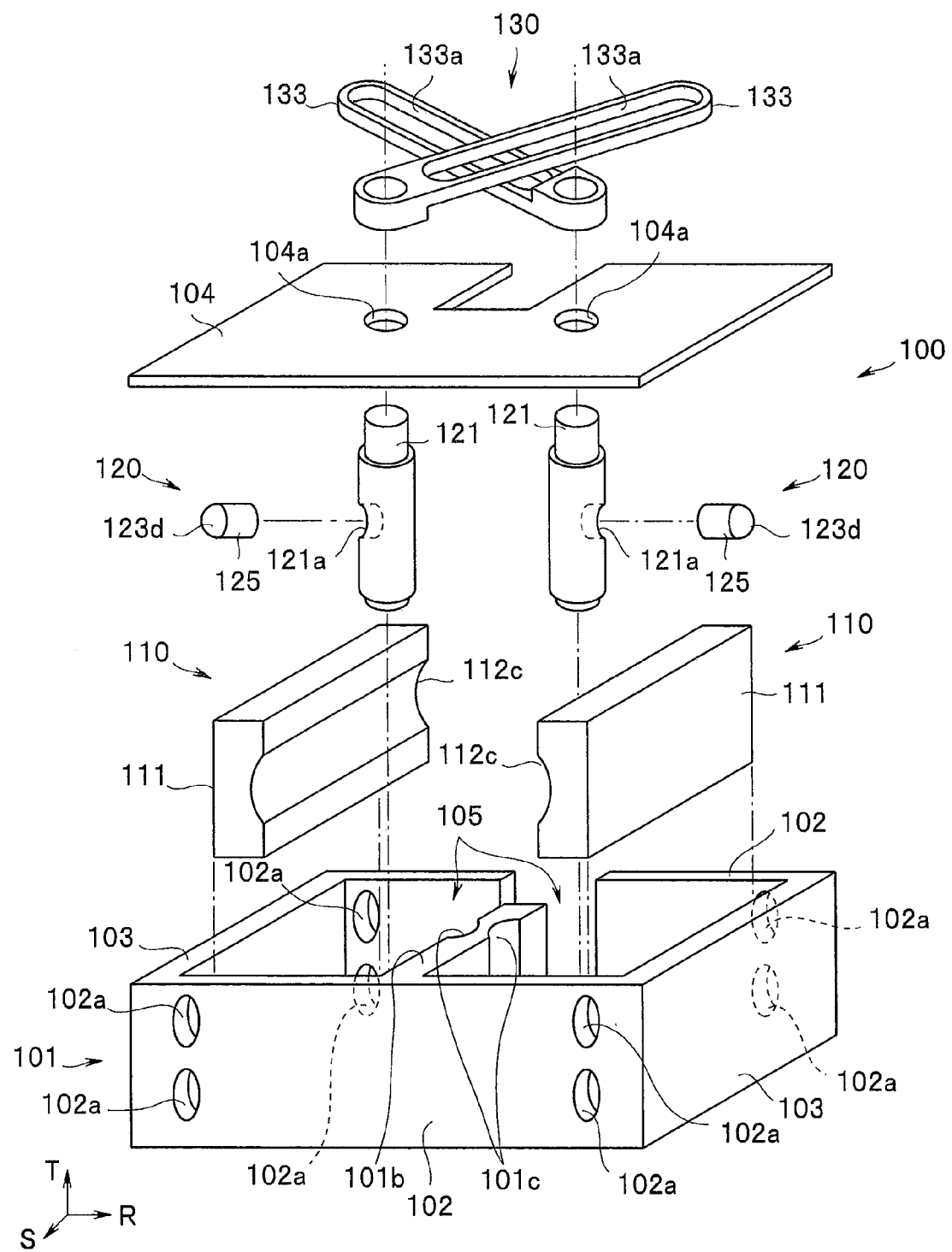
FIG. 19 is an exploded perspective view illustrating main parts of a linear member fixing mechanism according to a sixth embodiment of the present invention.
Figure 20:
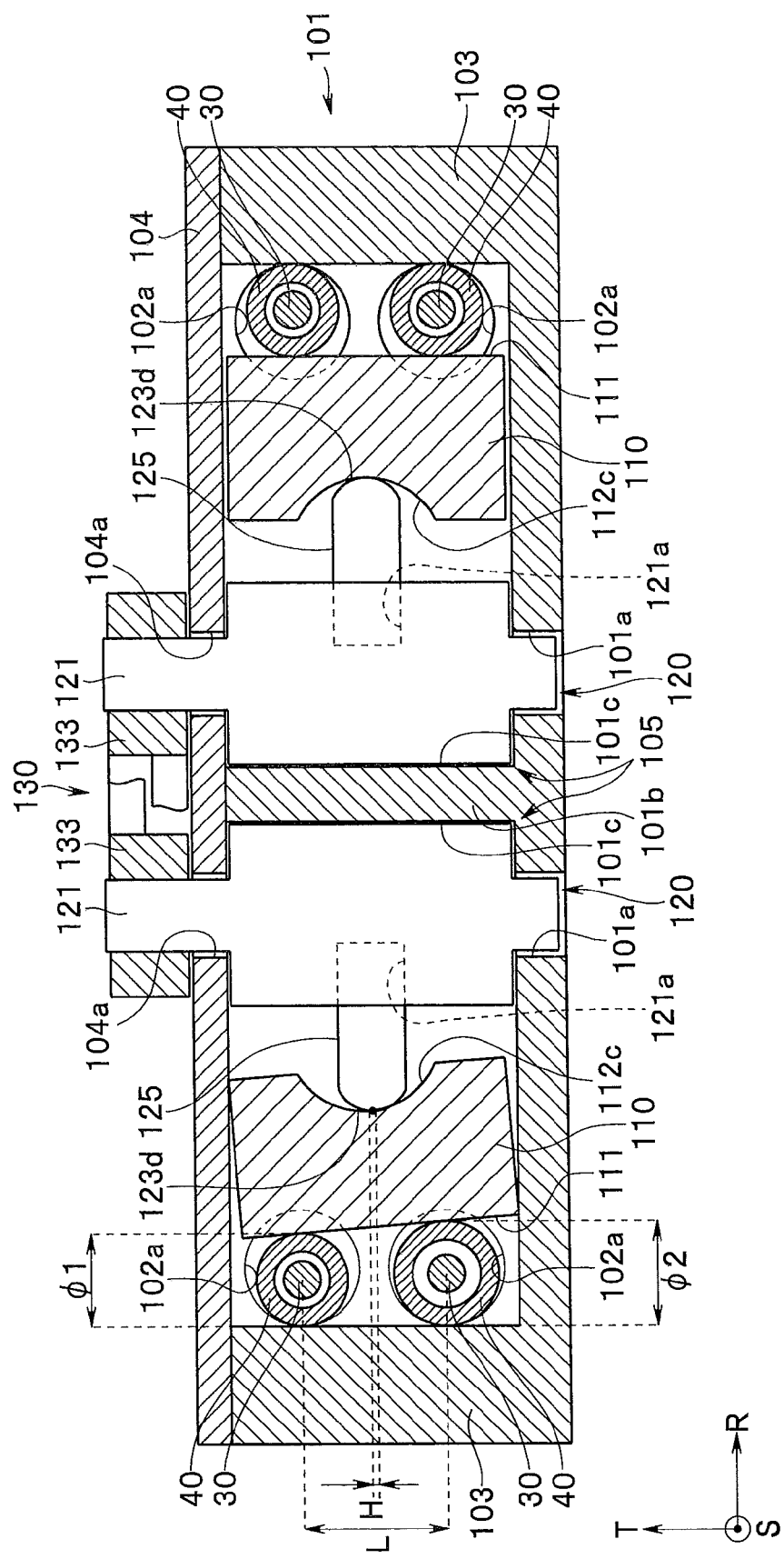
FIG. 20 is a cross-sectional view of main parts of the linear member fixing mechanism according to the sixth embodiment of the present invention.

FIGS. 19 and 20 relate to the sixth embodiment of the present invention. FIG. 19 is an exploded perspective view illustrating main parts of the linear member fixing mechanism. FIG. 20 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 19 and 20, the face to be pressed 112*c* that is formed of a concave curved face that bends along the interaxial direction T of two of the inner guide sheaths 40 and that has a bottom portion between the axes of the two inner guide sheaths 40 is set on a rear face side of the contact face 111 in the respective braking members 110.

On the other hand, a hole portion 121*a* that corresponds to the face to be pressed 112*c* and opens in a direction perpendicular to the axis is provided in the camshaft 121 of each eccentric cam 120. A convex member 125 formed of a separate member is fixedly provided in the hole portion 121*a*. A hemispherical face, for example, is formed at a distal end portion of the convex member 125, and the hemispherical face is set as a cam face 123*d*.

By constituting the face to be pressed 112*c* by means of a concave curved face and setting the cam face 123*d* at the distal end portion of the convex member 125, as shown in FIG. 20, contact between the face to be pressed 112*c* and the cam face 123*d* in the interaxial direction T of two of the inner guide sheaths 40 is set so that the contact width H thereof is shorter than an interaxial distance between the two inner guide sheaths 40 and the contact position is located between the axes of the two inner guide sheaths 40.

According to this embodiment, in addition to the advantageous effects obtained by the foregoing first embodiment, an advantageous effect can also be obtained that tuning or the like of a pressing force characteristic of the eccentric cams 120 can be easily implemented by replacing the convex members 125. Further, by forming only the convex members 125 using a material with high wear resistance, eccentric cams 120 that have a high level of durability can be realized without lowering the workability and the like of the eccentric cams 120 overall.

Note that, in the present embodiment, the respective faces to be pressed need not necessarily be constituted by a concave curved face.

Further, although an example in which a convex member is fixedly provided in each of the eccentric cams 120 is described in the above embodiment, it is also possible to adopt a configuration in which, instead of fixedly providing a convex member in each of the eccentric cams 120, for example, a convex member is fixedly provided in the respective braking members 110, and a face to be pressed is set at an end portion of the respective convex members. In this case, for example, the cam member 122 or the like described in the foregoing first embodiment can be provided in the eccentric cam 120.

Figure 21:
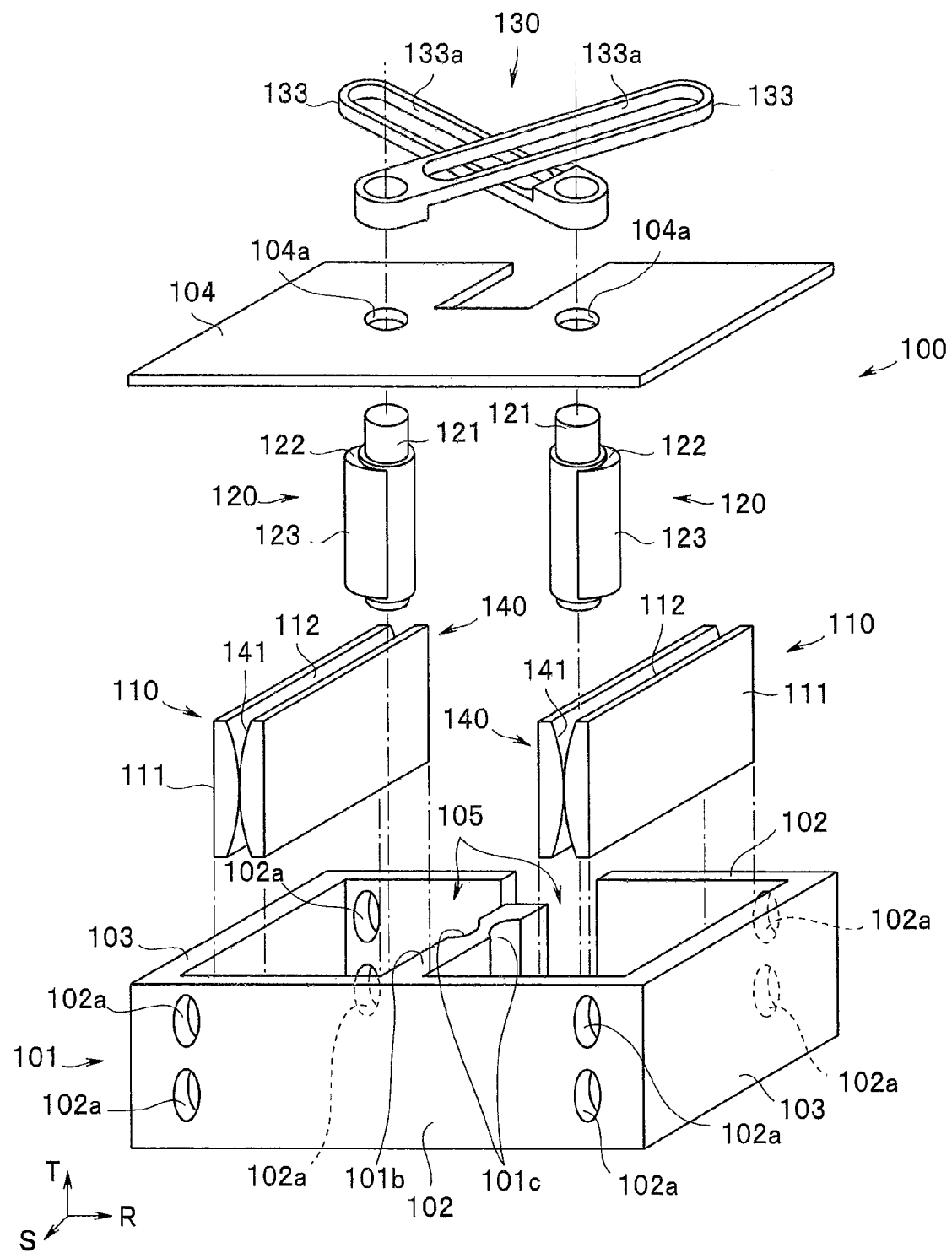
FIG. 21 is an exploded perspective view illustrating main parts of a linear member fixing mechanism according to a seventh embodiment of the present invention.
Figure 22:
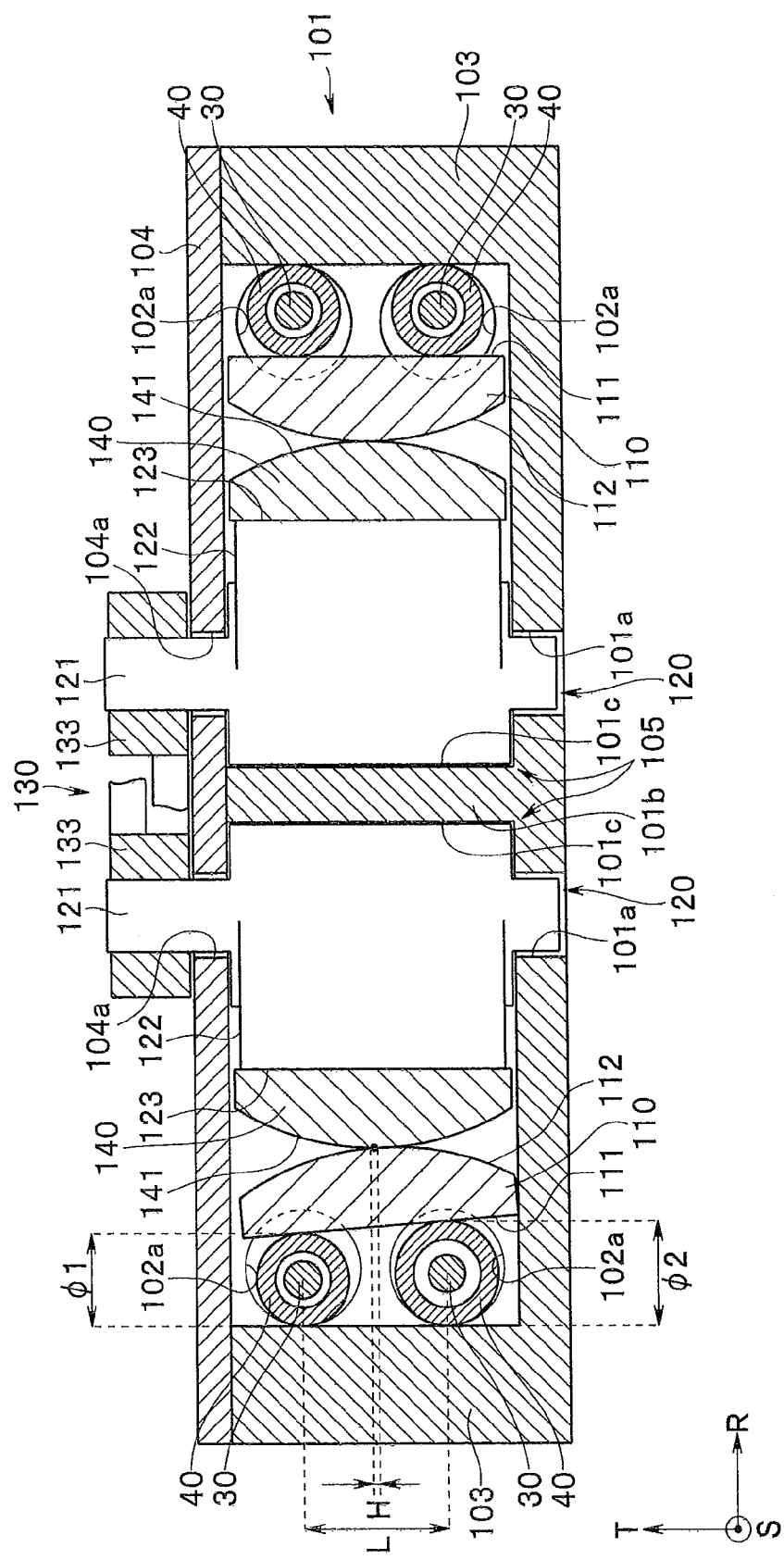
FIG. 22 is a cross-sectional view of main parts of the linear member fixing mechanism according to the seventh embodiment of the present invention.

FIGS. 21 and 22 relate to the seventh embodiment of the present invention. FIG. 21 is an exploded perspective view illustrating main parts of the linear member fixing mechanism. FIG. 22 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 21 and 22, an intermediate member 140 is interposed between each braking member 110 and the corresponding eccentric cam 120. The intermediate member 140 is, for example, formed of a plate-like member that extends along the longitudinal axis direction S inside the brake chamber 105. A face 141 that faces the braking member 110 of the intermediate member 140 is constituted by a convex curved face that bends along the interaxial direction T of two of the inner guide sheaths 40 and has a top portion between the axes of the two inner guide sheaths 40. According to the present embodiment, instead of the cam faces 123 of the respective eccentric cams 120, the face 141 that faces the braking member 110 of each intermediate member 140 functions as a pressing face that can contact the face to be pressed 112.

As shown in FIG. 22, contact between the face to be pressed 112 and the facing face 141 in the interaxial direction T of two of the inner guide sheaths 40 is set so that a contact width H thereof is shorter than the interaxial distance L between the two inner guide sheaths 40 and the contact position is located between the axes of the two inner guide sheaths 40.

According to this embodiment, in addition to the advantageous effects obtained by the foregoing first embodiment, an advantageous effect can also be obtained that tuning or the like of a pressing force characteristic of the eccentric cams 120 can be easily implemented by replacing the intermediate members 140. Further, the durability of the eccentric cams 120 can be improved by forming the intermediate members 140 using a material with high wear resistance.

Note that, although an example in which a pressing face that can contact with a face to be pressed is set as an intermediate member is described in the above embodiment, it is also possible to adopt a configuration in which, for example, surface contact between the respective braking members 110 and the respective intermediate members 140 is contact between flat surfaces, a convex curved face is formed on a face that faces the eccentric cam 120 of the intermediate member 140, and the convex curved face is set as the face to be pressed.

Figure 23:
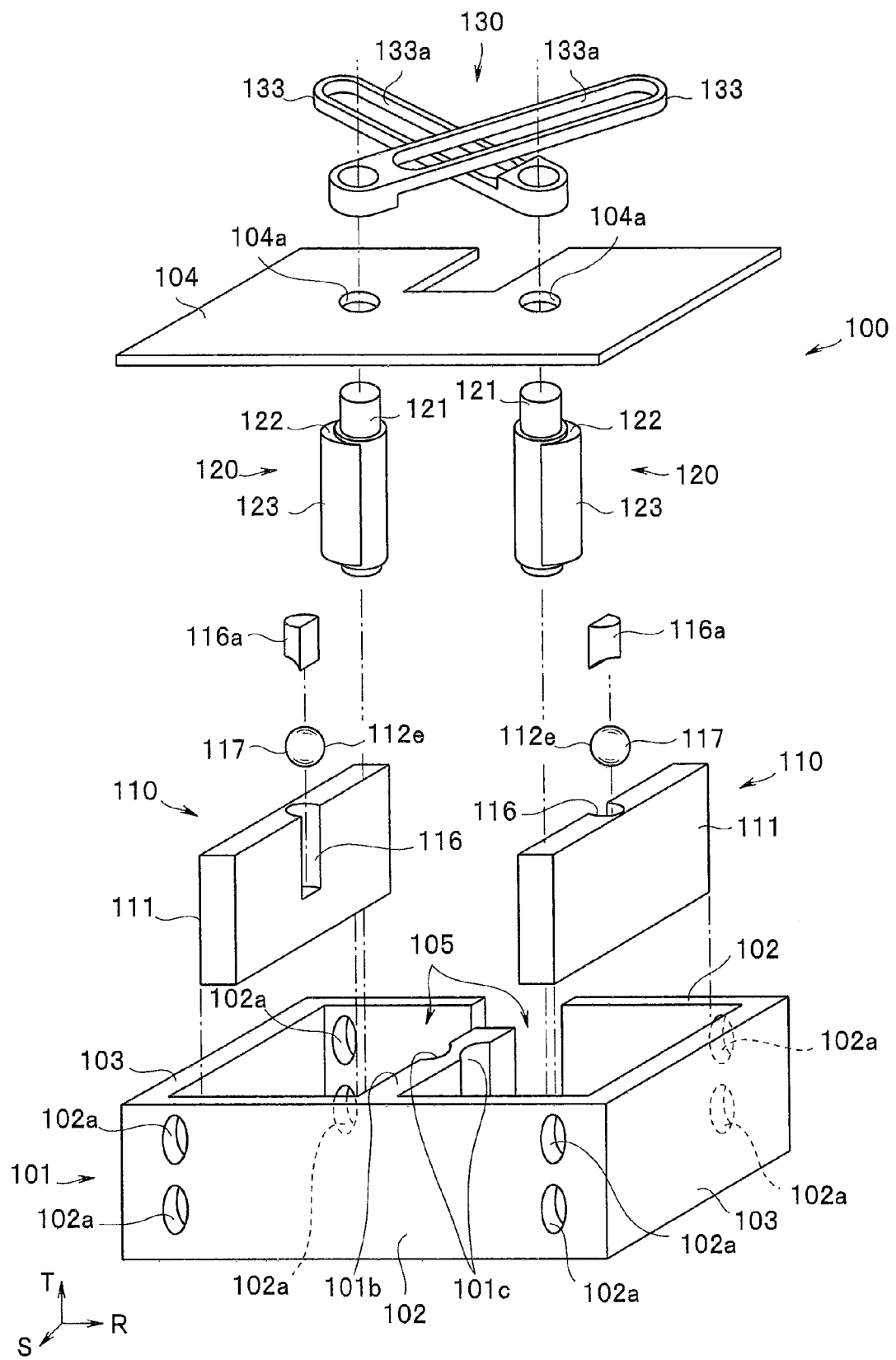
FIG. 23 is an exploded perspective view illustrating main parts of a linear member fixing mechanism according to an eighth embodiment of the present invention.
Figure 24:
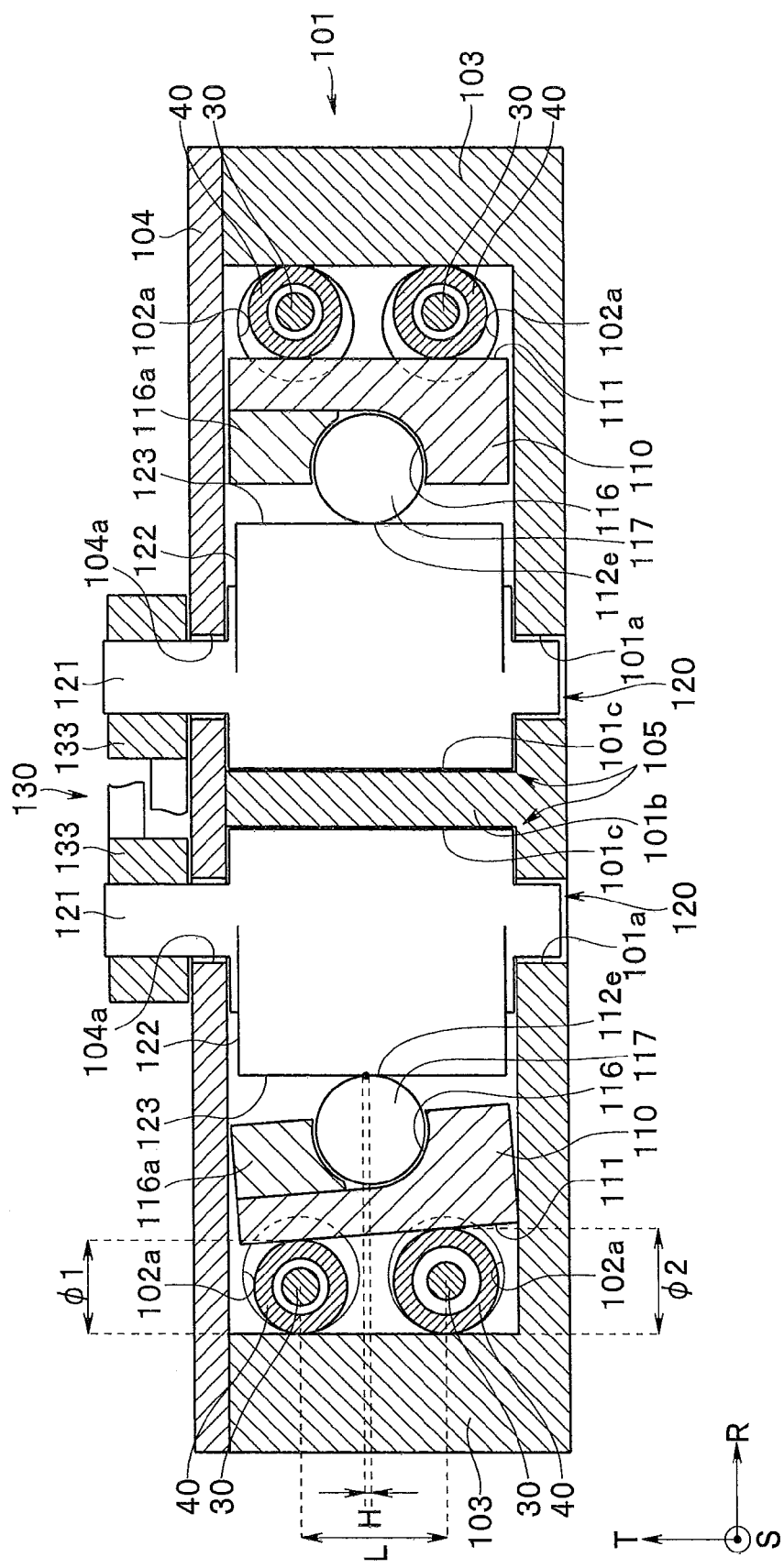
FIG. 24 is a cross-sectional view of main parts of the linear member fixing mechanism according to the eighth embodiment of the present invention.

FIGS. 23 and 24 relate to the seventh embodiment of the present invention. FIG. 23 is an exploded perspective view illustrating main parts of the linear member fixing mechanism. FIG. 24 is a cross-sectional view of main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 23 and 24, an arcuate groove portion 116 is provided in the rear face side of the contact face 111 of each braking member 110. A spherical body 117 is rollably housed in the groove portion 116. The spherical body 117 is prevented from coming out of the groove portion 116 by a stopper member 116*a* that is fitted into the groove portion 116. One portion of the spherical body 117 is exposed from the braking member 110. The exposed portion of the spherical body 117 is set as a face to be pressed 112*e*.

Further, as shown in FIG. 24, contact between the face to be pressed 112*e* and the cam face 123 in the interaxial direction T of two of the inner guide sheaths 40 is set so that the contact width H thereof is shorter than the interaxial distance L between the two inner guide sheaths 40 and the contact position is located between the axes of the two inner guide sheaths 40.

According to this embodiment, in addition to the advantageous effects of the foregoing first embodiment, by using the spherical body 117 to constitute the face to be pressed 112*e*, an advantageous effect can also be obtained that the braking member 110 can be tilted in an arbitrary direction in accordance with the state of the inner guide sheaths 40. Accordingly, the contact face 111 can be caused to accurately contact with a wide area of the respective inner guide sheaths 40 not only in a case where the external diameters of two inner guide sheaths 40 are different to each other, but also in a case where the external diameter in the insertion direction S of the inner guide sheaths 40 changes.

Note that although an example in which the spherical body 117 is held on the braking member 110 side and set as the face to be pressed 112e has been described in the above embodiment, it is also possible to adopt a configuration in which, for example, a spherical body is held on the eccentric cam 120 side and set as a pressing face.

Figure 25:
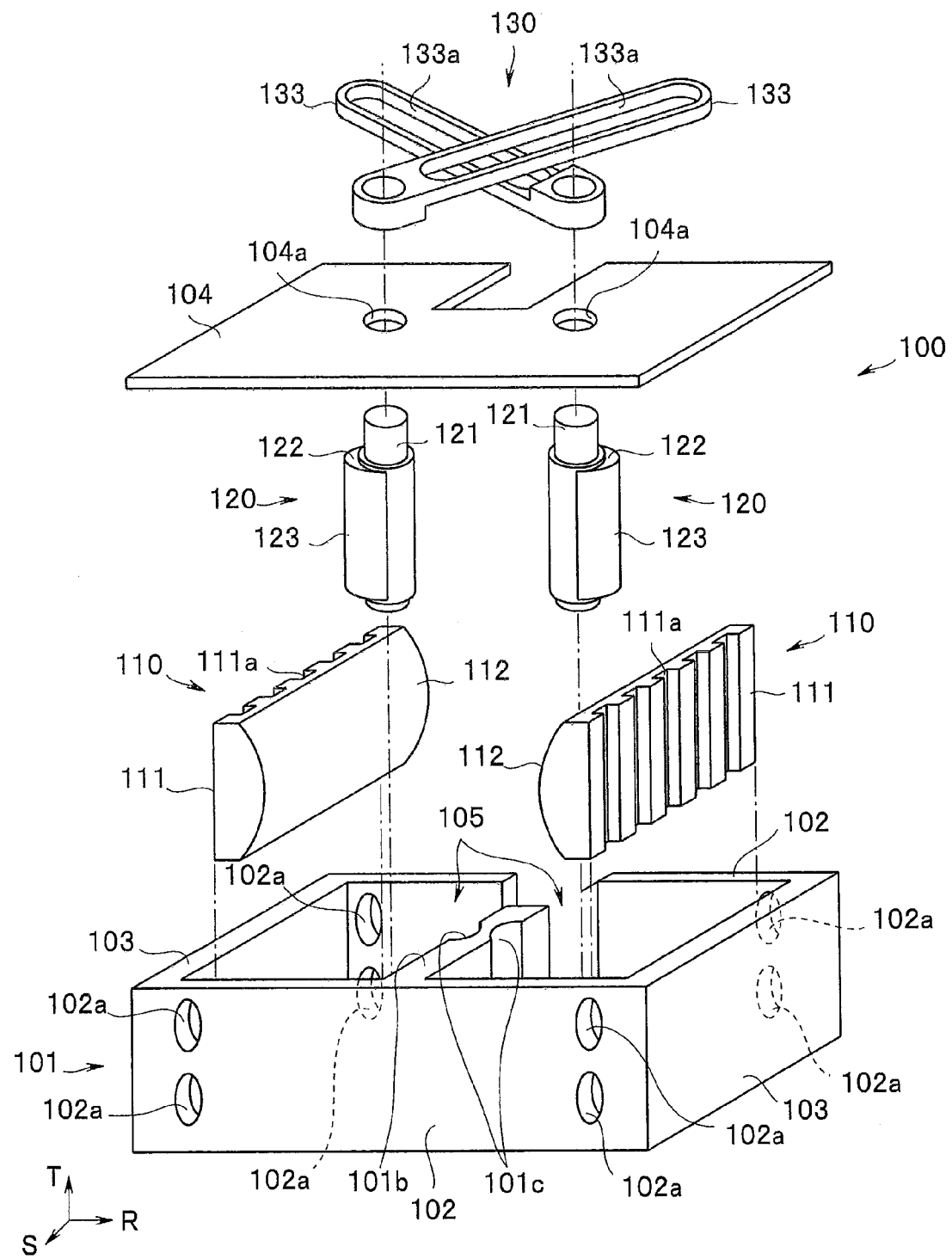
FIG. 25 is an exploded perspective view illustrating main parts of a linear member fixing mechanism according to a ninth embodiment of the present invention.
Figure 26:
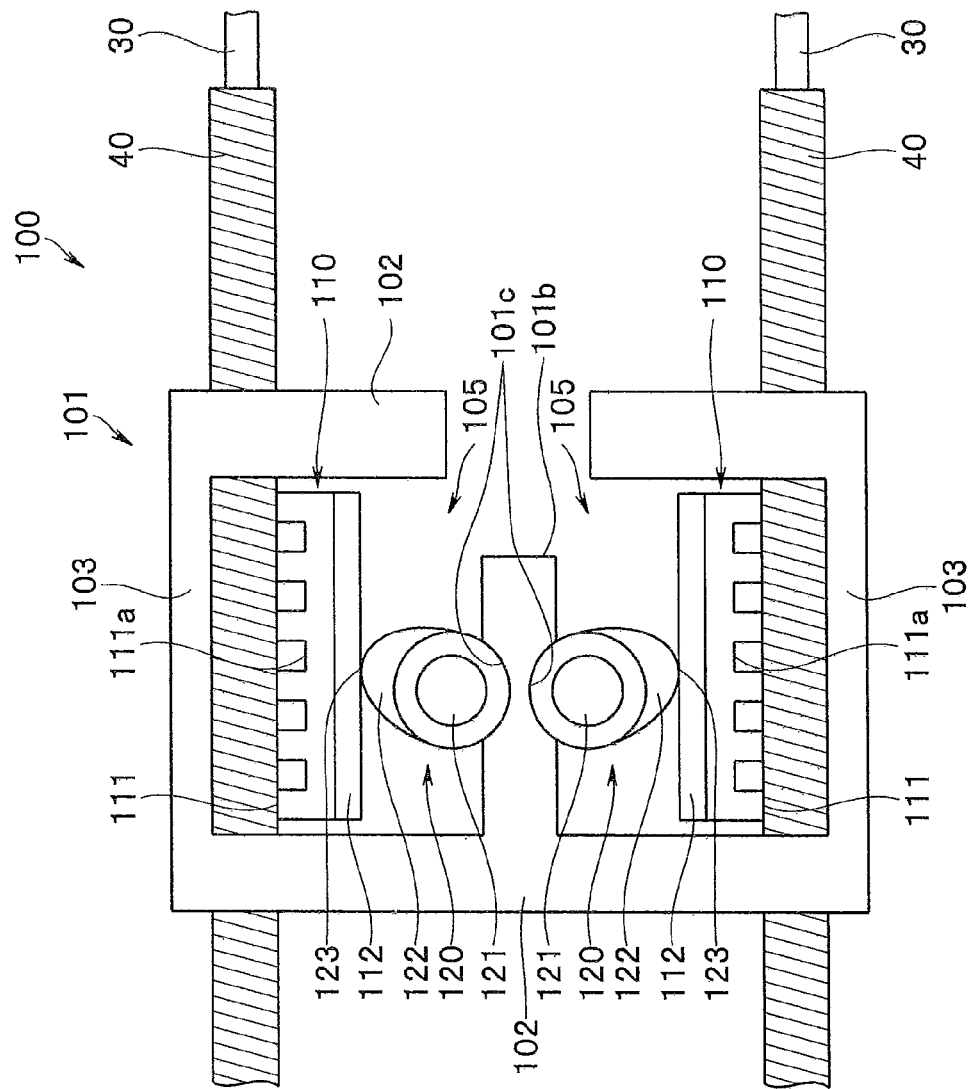
FIG. 26 is a plan view illustrating main parts of the linear member fixing mechanism according to the ninth embodiment of the present invention.

FIGS. 25 and 26 relate to the seventh embodiment of the present invention. FIG. 25 is an exploded perspective view illustrating main parts of the linear member fixing mechanism. FIG. 26 is a plan view showing main parts of the linear member fixing mechanism. Note that, in the present embodiment, the main difference relative to the above described first embodiment is the configuration of the braking members and the eccentric cams. In addition, components that are the same as in the foregoing first embodiment are denoted by the same reference characters and a description of such components is omitted.

As shown in FIGS. 25 and 26, concave grooves 111a are provided at a predetermined pitch in the contact face 111 of the respective braking members 110. Thus, the contact face 111 is formed in a discontinuous manner in the longitudinal axis direction S.

According to this embodiment, by forming the contact face 111 with a discontinuous face in the longitudinal axis direction S, the inner guide sheaths 40 can be accurately held with a smaller pressing force.

Note that the present invention is not limited to the respective embodiments described above, and various modifications and changes are possible, and such changes and modifications are also within the technical scope of the present invention. For example, naturally the configurations of the respective embodiments described above may be appropriately combined.

Further, application of the present invention is not limited to an endoscope, and the present invention may also be applied to other insertion instruments such as a guide tube, various kinds of treatment instruments, and a manipulator, as long as the insertion instrument has an action portion at a distal end of an insertion portion. Furthermore, with respect to the action portion also, the action portion is not limited to a bending portion, and may be another action portion such as a forceps raising base provided inside a distal end portion of an insertion portion. In addition, although an example in the case of simultaneously fixing four linear members is described in each of the foregoing embodiments, the present invention is not limited thereto. For example, the present invention can also be applied to one set of linear members that form a pair of two adjacent linear members or to two or more sets of linear members. Further, with respect to the linear members also, the present invention can also be applied to wires for bending and wires that raise a forceps raising base and the like.

What is claimed is:

1. An insertion instrument, comprising:
    an insertion portion for inserting into a subject;
    an operation portion that is provided on a proximal end side of the insertion portion;
    an action portion that is provided in the insertion portion and that acts in accordance with an operation input with respect to the operation portion;
    two linear members that are arranged such that a part of proximal ends of the two linear members are adjacent to each other along a planar wall face formed in the operation portion, and that move in a longitudinal axis direction of the insertion portion in response to the operation input at the operation portion to transmit the operation input at the operation portion to the action portion;
    a braking member that includes, at a position facing the wall face, a contact face for contacting the two linear members, and which is disposed in a state in which the braking member is movable in an approximately perpendicular direction with respect to a movement direction and an interaxial direction of the two linear members and in which the contact face is tiltable in the interaxial direction of the two linear members with respect to the wall face;
    a face to be pressed that is provided on a rear face side of the contact face of the braking member; and
    a pressing member for pressing the face to be pressed in the approximately perpendicular direction.

2. The insertion instrument according to claim 1, wherein a contact width between the face to be pressed and a pressing face of the pressing member that is capable of contacting the face to be pressed in the interaxial direction of the two linear members is set to be shorter than an interaxial distance between the two linear members, and a contact position between the face to be pressed and the pressing face is set between axes of the two linear members.

3. The insertion instrument according to claim 1, wherein a portion at which the face to be pressed and a pressing face of the pressing member that is capable of contacting the face to be pressed come in contact has a configuration that tilts the contact face of the braking member to which a pressing force is applied from the pressing member and causes the contact face to come in contact with the respective linear members.

4. The insertion instrument according to claim 1, comprising:
    operation input means provided on the operation portion;
    an eccentric cam as the pressing member; and
    a link mechanism having a connecting arm that converts an operation input with respect to the operation input means into a rectilinear advancing movement of a slider, and a cam lever that converts the rectilinear advancing movement of the slider into a rotational movement of the eccentric cam.

5. The insertion instrument according to claim 1, wherein:
    either one of the face to be pressed and a pressing face of the pressing member that is capable of contacting the face to be pressed comprises a convex curved face that bends along the interaxial direction of the two linear members and that has a top portion between axes of the two linear members; and
    the other of the face to be pressed and the pressing face comprises a flat face along the interaxial direction of the two linear members.

6. The insertion instrument according to claim 1, wherein:
    the face to be pressed and a pressing face of the pressing member that is capable of contacting the face to be pressed comprise a flat face along the interaxial direction of the two linear members; and
    a width in the interaxial direction of the two linear members of either one of the face to be pressed and the pressing face is set to be shorter than an interaxial distance between the two linear members.

7. The insertion instrument according to claim 1, wherein:
    the face to be pressed is set to a convex portion that is provided on the braking member;

a pressing face of the pressing member that is capable of contacting the face to be pressed is set to a convex portion that is provided on the pressing member; and at least either one of the face to be pressed and the pressing face comprises a convex curved face that bends along the interaxial direction of the two linear members and that has a top portion between axes of the two linear members.

8. The insertion instrument according to claim 1, wherein:

the face to be pressed comprises a concave curved face that bends along the interaxial direction of the two linear members and that has a bottom portion between axes of the two linear members; and a pressing face of the pressing member that is capable of contacting the face to be pressed is set to a convex portion that is provided on the pressing member, and comprises a convex curved face that bends along the interaxial direction of the two linear members and that has a top portion between axes of the two linear members.

9. The insertion instrument according to claim 1, wherein:

the face to be pressed is set to a convex portion that is provided on the braking member; and a pressing face of the pressing member that is capable of contacting the face to be pressed is set to a concave portion that is provided on the pressing member.

10. The insertion instrument according to claim 1, wherein a convex member comprising a separate member is fixedly provided in the braking member, and the face to be pressed that is capable of contacting a pressing face provided on the pressing member is set to an end portion of the convex member.

11. The insertion instrument according to claim 1, wherein an intermediate member is interposed between the braking member and the pressing member, and a pressing face that transmits a pressing force from the pressing member and the face to be pressed that is capable of contacting the pressing face and to which the pressing force is transmitted are set to the intermediate member.

12. The insertion instrument according to claim 1, wherein a spherical body is held in the braking member or in the pressing member, and a pressing face that transmits a pressing force from the pressing member and the face to be pressed that is capable of contacting the pressing face and to which the pressing force is transmitted are set to the spherical body.

13. The insertion instrument according to claim 1, wherein a convex member comprising a separate member is fixedly provided in the pressing member, and a pressing face that is provided to be capable of contacting the face to be pressed is set to an end portion of the convex member.

* * * * *